(12) United States Patent
Kendall et al.

(10) Patent No.: US 10,391,494 B2
(45) Date of Patent: Aug. 27, 2019

(54) SWAB CANISTER EQUIPPED WITH MOISTURE PERMEABLE MEMBRANE AND DESSICANT

(71) Applicant: Signature Science, LLC, Austin, TX (US)

(72) Inventors: John Kirby Kendall, Cedar Park, TX (US); Alyse N. Hilton, Mosely, VA (US); Elayna W. Moreithi, Charlottesville, VA (US); Carmen R. Reedy, Charlottesville, VA (US); Erica L. Toy, Charlottesville, VA (US)

(73) Assignee: Signature Science, LLC, Austin, TX (US)

( * ) Notice: Subject to any disclaimer, the term of this patent is extended or adjusted under 35 U.S.C. 154(b) by 222 days.

(21) Appl. No.: 15/444,327

(22) Filed: Feb. 27, 2017

(65) Prior Publication Data

US 2017/0248498 A1   Aug. 31, 2017

Related U.S. Application Data

(60) Provisional application No. 62/299,631, filed on Feb. 25, 2016.

(51) Int. Cl.
| | | |
|---|---|---|
| *B01L 3/00* | | (2006.01) |
| *G01N 1/02* | | (2006.01) |
| *A61L 2/20* | | (2006.01) |
| *A61L 2/04* | | (2006.01) |
| *A61L 2/07* | | (2006.01) |
| *A61L 2/08* | | (2006.01) |

(52) U.S. Cl.
CPC ............ *B01L 3/5029* (2013.01); *A61L 2/206* (2013.01); *G01N 1/02* (2013.01); *A61L 2/04* (2013.01); *A61L 2/07* (2013.01); *A61L 2/08* (2013.01); *A61L 2/202* (2013.01); *A61L 2/208* (2013.01); *A61L 2202/23* (2013.01); *B01L 2200/0689* (2013.01); *B01L 2200/141* (2013.01); *B01L 2300/042* (2013.01); *B01L 2300/069* (2013.01); *B01L 2300/105* (2013.01); *G01N 2001/028* (2013.01)

(58) Field of Classification Search
CPC ........................ B01L 3/5029; G01N 2001/028
See application file for complete search history.

(56) References Cited

U.S. PATENT DOCUMENTS

| | | | | |
|---|---|---|---|---|
| 2004/0062693 A1* | 4/2004 | Lin | ........................... | A61L 2/07 422/297 |
| 2005/0112547 A1* | 5/2005 | Youngkin | ................ | C12Q 1/04 435/4 |
| 2012/0220043 A1* | 8/2012 | Sangha | .................... | G01N 1/02 436/174 |

* cited by examiner

*Primary Examiner* — Donald R Spamer
(74) *Attorney, Agent, or Firm* — John A. Fortkort; Fortkort & Houston PC

(57) ABSTRACT

A swab canister (101) is provided which includes a container (103) equipped with a first opening (105) and having a removable sample collector (117) disposed therein. A membrane (111) which is permeable to both moisture and a sanitizing agent such as ethylene oxide is disposed between the sample collector and the first opening. A desiccant (113) disposed between the membrane and the first opening.

20 Claims, 49 Drawing Sheets

Water ampoule ready to be twisted off (1)

SWAB CANISTER EQUIPPED WITH MOISTURE PERMEABLE MEMBRANE AND DESSICANT

FIELD OF THE DISCLOSURE

The present disclosure relates generally to sampling devices, and more particularly to a swab canister equipped with a moisture permeable membrane and desiccant which inhibits bacterial growth in a specimen swab, and which reduces or eliminates the contamination of specimens with foreign DNA.

BACKGROUND OF THE DISCLOSURE

Forensic analysis frequently requires that evidence be captured and preserved until it can be analyzed in a laboratory setting or presented to a court of law. Such evidence may include biological substances, such as blood, saliva, urine or semen, which may need to be identified and subjected to chemical and/or DNA analysis for identification or for association with a particular individual.

The use of fibrous swabs for collecting specimen samples has become ubiquitous in the forensic arts. Such swabs, which typically comprise cotton, not only absorb liquids (and solids suspended in liquids), but also effectively capture dry particulate substances.

Prior to use, the swabs are typically kept in closed, sterile containers known as swab canisters to avoid exposure to environmental contaminants. Similarly, after a swab has been used to collect a specimen, it is typically placed in a sterile bag or container to avoid contamination during subsequent handing. In order to establish a chain of custody of the sample, it is common to mark the bag or container with appropriate information. Such information may include, for example, the time, date and location at which the sample was collected, the identity of the party who collected the sample, and a unique sample identifier. The bag or container containing the swab may also be provided with a desiccant to remove any excess moisture present in the sample, since such moisture can promote the growth of bacteria in the sample. Left unchecked, such bacterial growth can lead to sample degradation, which can complicate forensic analysis and potentially render the sample useless.

Sample swabs may also become contaminated during use as a result of careless handling. For example, an investigator at a crime scene may put a swab down after it has been used to collect a sample, but before the swab has been placed in a sterile bag or container. This may occur, for example, while the investigator is opening a bag or container into which the swab will be placed, or is allowing the swab to dry. During this time, the swab may become contaminated as a result of coming into contact with one or more surfaces.

Various devices and methodologies have been proposed in the art to reduce or minimize the contamination of sample swabs during use. For example, U.S. Pat. No. 8,940,547 (Sangha) and U.S. Pat. No. 9,052,254 (Sangha), FIGS. 1-2 of which have been reproduced as FIGS. 1-2 herein, disclose a swab-based evidence collecting apparatus 10 which features a shaft 16 having a swab 14 mounted on a first end thereof. A second end of the shaft 16 is connected to a closure 18. The closure 18 comprises a central member 20 having a stopper 22a, 22b which extends from each of the opposing sides of the central member.

The specimen collector 12 further includes a rigid break-off tube 24 which is mounted coaxially on the shaft 16. A first end of the tube 24 is connected to the closure 18. A second end of the tube 24 is configured to terminate at a selected location along the shaft 16 at which the shaft may be broken in order to achieve separation of the swab 14 from the remainder of the apparatus 10.

Closure 18 comprises a central member 20 and is equipped with a stopper 22a, 22b extending from each of the two opposing sides of the central member 20. The apparatus 10 is depicted with the stopper 22a having a shaft 16 and tube 24 connected thereto, and with the stopper 22b inserted into the neck 26 of the housing 28 of the apparatus 10.

FIG. 1 depicts the apparatus 10 in an open position in which the specimen collector 12 has been removed from housing 28, and in which the closure 18 has been reversed and inserted into opening 30 (see FIG. 2) of the neck 26 of housing 28 from which the specimen collector 12 was just removed. This reversal and insertion allows the housing 28 to act as a handle for manipulating the swab 14 of specimen collector 12 during the collection of a specimen. The relatively large, flat surface of desiccant chamber 32 fits securely into the palm of the hand and prevents the apparatus 10 from moving when it is placed on a surface. When positioned on a surface, the edge of the closure 18 extends laterally beyond the swab 14 and keeps the swab 14 separated from any contact with adjacent contaminating surfaces. In the closed position, the specimen collector 12 is inserted into the housing 28 and the stopper 22a of closure 18 is inserted into the opening 30 (see FIG. 2).

As seen in FIG. 2, the housing 28 includes a desiccant chamber 32 which is connected to the neck 26 of the housing 28. The desiccant chamber 32 is equipped with a resealable cover 34 that forms the bottom of the housing 28. The cover 34 may be generally flat to allow the apparatus 10 to stand on a surface. The cover 34 may be removably connected to desiccant chamber 32, or it may be permanently sealed to close chamber 32.

As seen in FIG. 2, the desiccant chamber 32 is equipped with fixed retainers 38 that hold desiccant packets 36 in position therein. When the swab 14 is positioned within the housing 28, it is situated between the retainers 38 in a swab isolation area 41, with the retainers 38, 40 holding the desiccant packets 20 away from the swab 14.

SUMMARY OF THE DISCLOSURE

In one aspect, an apparatus is provided which comprises (a) a container equipped with a first opening and having a removable sample collector disposed therein; (b) a membrane disposed between said sample collector and said first opening, wherein said membrane is permeable to both ethylene oxide and $H_2O$; and (c) a desiccant disposed between said membrane and said first opening.

DETAILED DESCRIPTION

Despite the care taken in the art to prevent contamination of sample swabs during storage, handling and use, swab contamination remains a persistent issue in the art. Recently, exposure of these articles to foreign substances during manufacture has been identified as a significant source of contamination.

For example, several instances have occurred where biological materials detected on sample swabs were later found to have been introduced during manufacture of the swab canister. In one such case (see John M. Butler, "Advanced Topics in Forensic DNA Typing: Methodology: Methodology" (Elsevier, 2012) p.8), investigators in Europe spent 15 years chasing the so-called "German phantom," a purported serial offender whose DNA profile had appeared in a variety of crimes over the years. In 2008, the "offender" was discovered to be an elderly woman who worked in the packaging department of a manufacturer of collection swabs. In placing the swabs in their packages, the worker had inadvertently contaminated some of them with her own DNA.

Similarly, E. Archer et al., "Validation of a Dual Cycle Ethylene Oxide Treatment technique to remove DNA from Consumables Used in Forensic Laboratories", *Forensic Science International,* Genetics 4 (2010) 239-243, notes that, despite the fact that sample swabs and swab canisters are typically produced in clean room environments and undergo sterilization to remove detectable levels of viable bacteria, "these treatments do not necessarily remove trace levels of DNA and some DNA contamination during manufacture is unavoidable. This has been demonstrated by recovering DNA from consumables supplied as sterile where the DNA profile matches that of a manufacturer's employee."

It will be appreciated from the foregoing that contamination of sample swabs and swab canisters with foreign materials (and especially materials containing DNA) during manufacturing may lead to a considerable waste of resources by law enforcement and government agencies. This problem is exacerbated by the fact that these agencies are frequently already short on manpower and funding. It is thus desirable to treat the interior surfaces of swab canisters after manufacture and assembly such that any biological materials they are exposed to during manufacture are rendered biologically inactive. It is also desirable that this treatment degrades any biological materials present on the surfaces of the sample swabs and sample canisters such that these materials will not produce a significant footprint during DNA analysis of any sample collected with these articles.

As noted in the above referenced article by E. Archer et al., one method of achieving the foregoing objective is to treat the inside of the canister with a chemical agent such as ethylene oxide. Ethylene oxide is a gas which effectively penetrates porous materials, is a potent sanitizer, and degrades the genomic sequences of any biological materials it comes into contact with.

Figure 1:
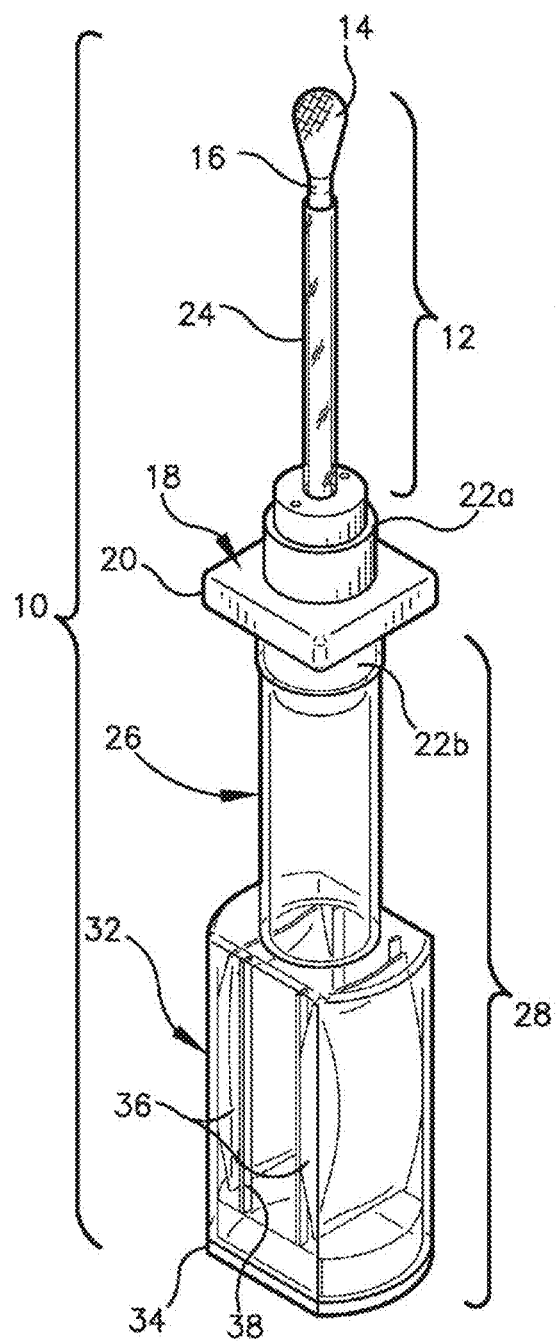
FIGS. 1-2 are perspective views of a prior art swab canister.
Figure 2:
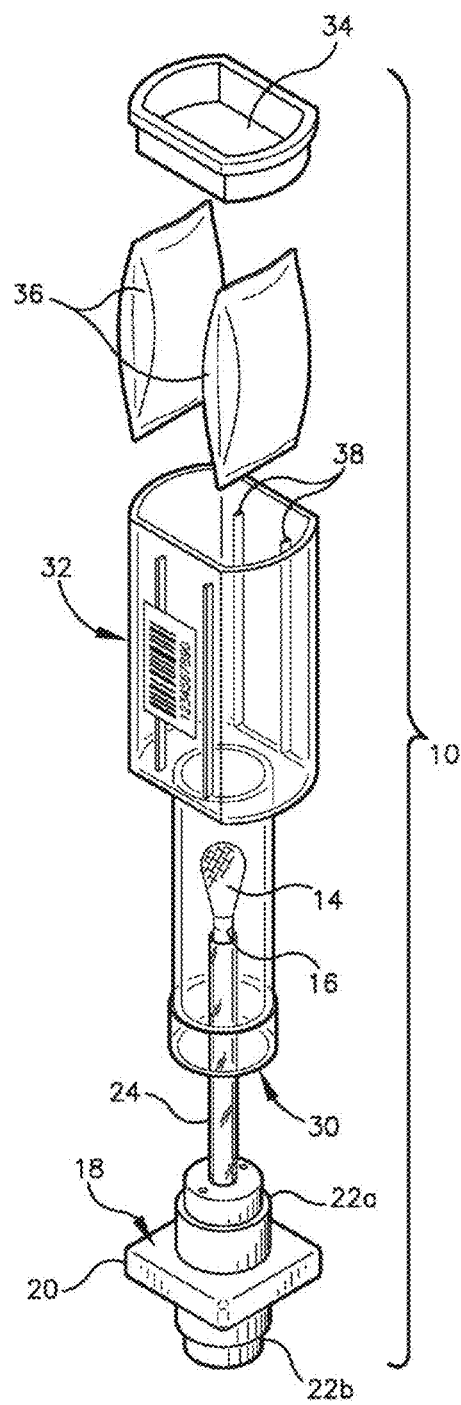
Figure 3:
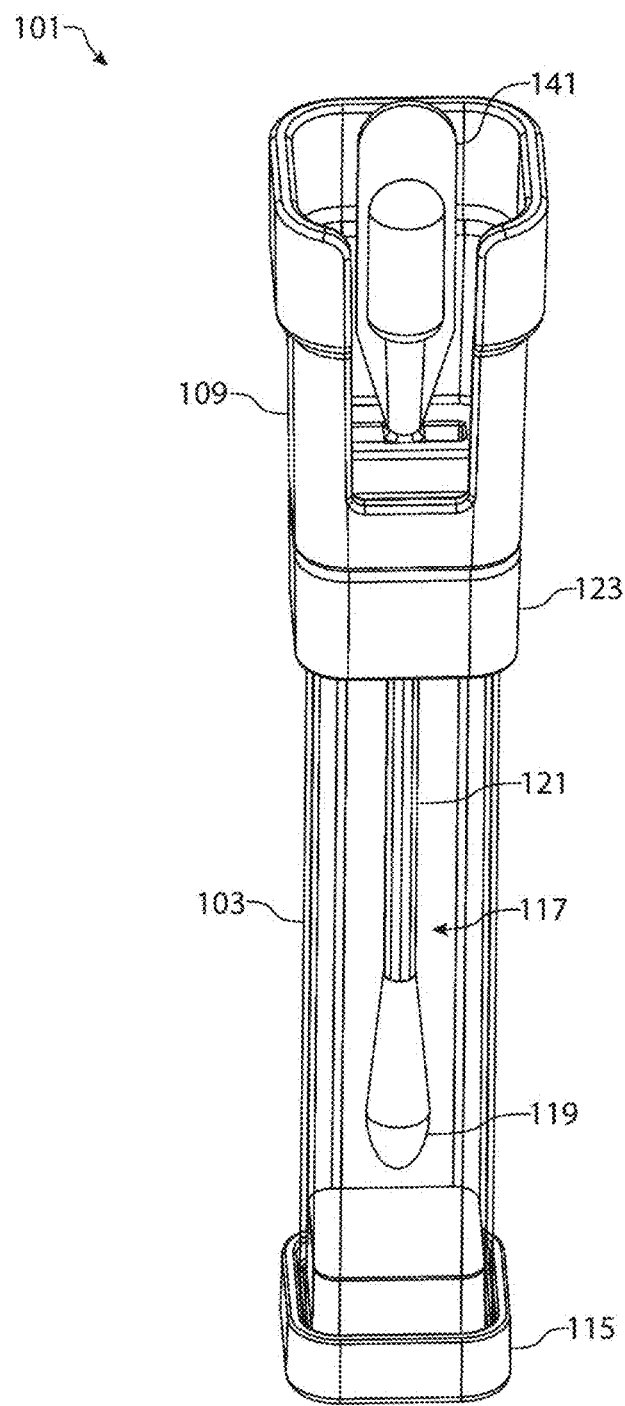
FIGS. 3-5 are perspective views of a first particular, non-limiting embodiment of a swab canister in accordance with the teachings herein.
Figure 4:
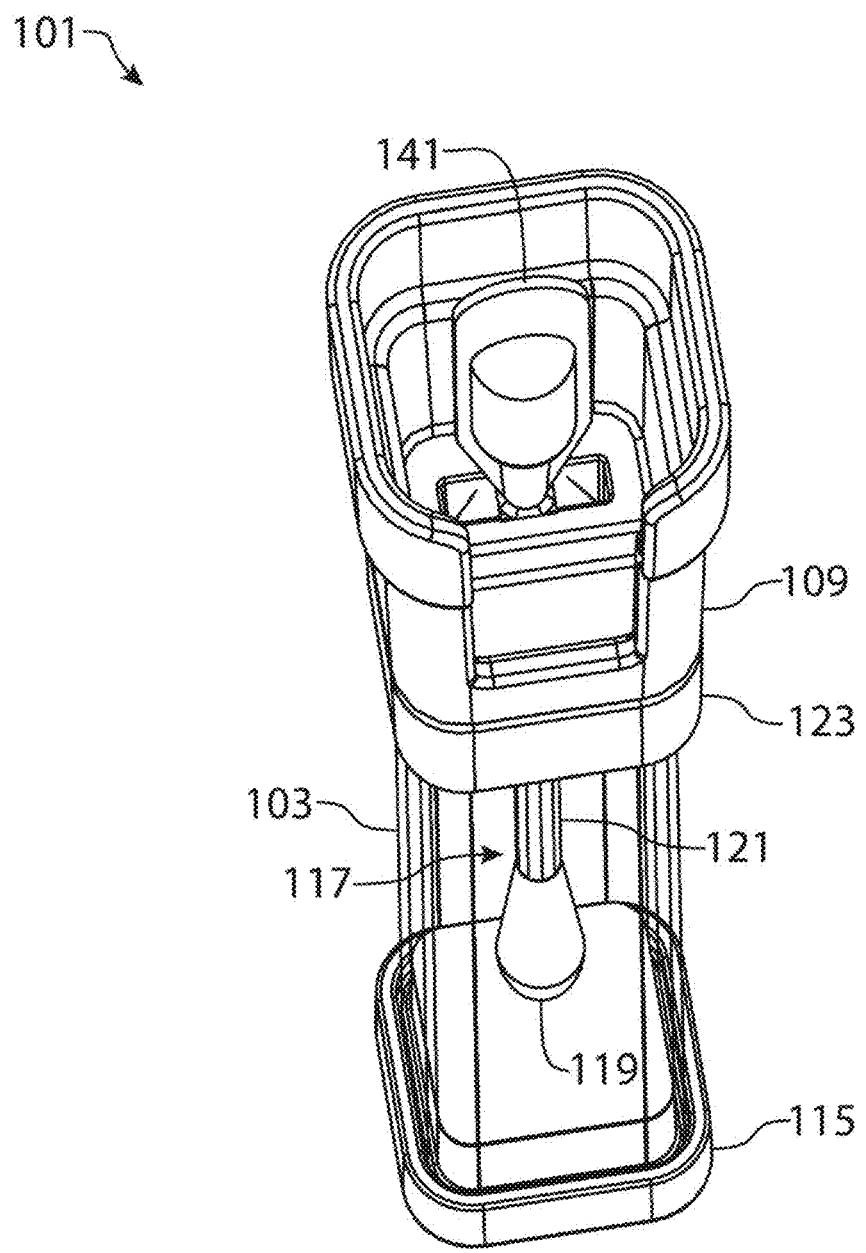
Figure 5:
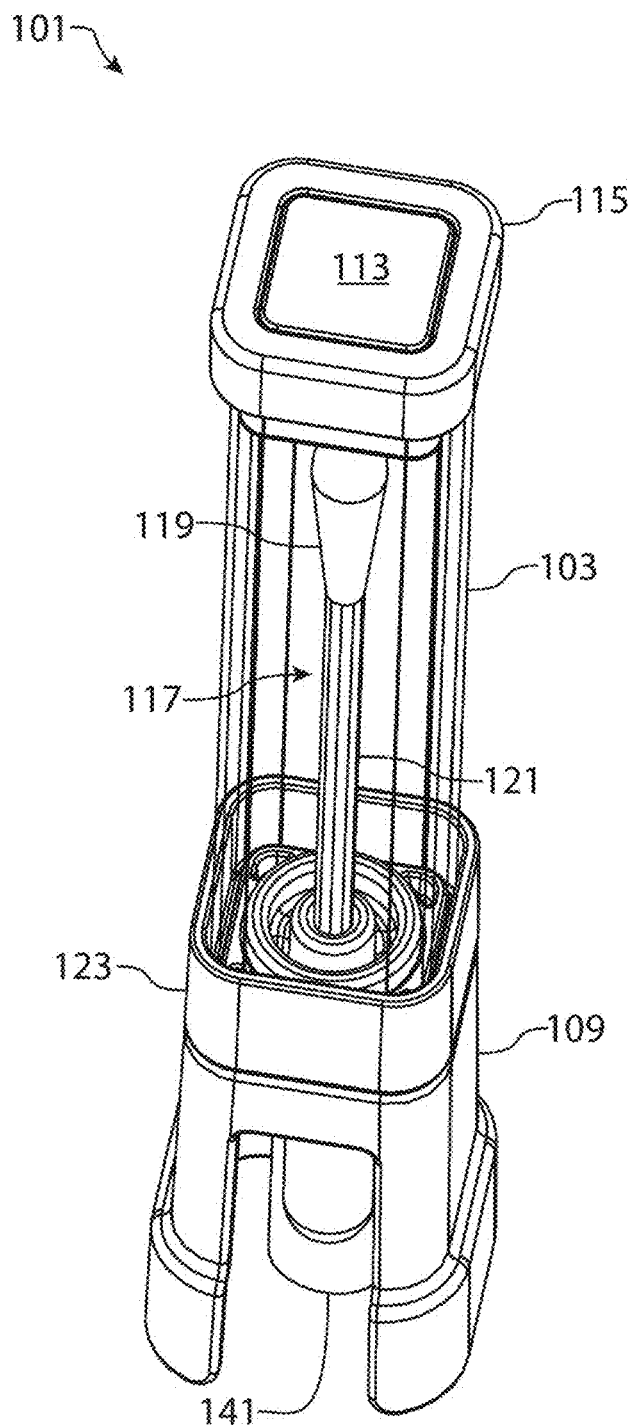
Figure 6:
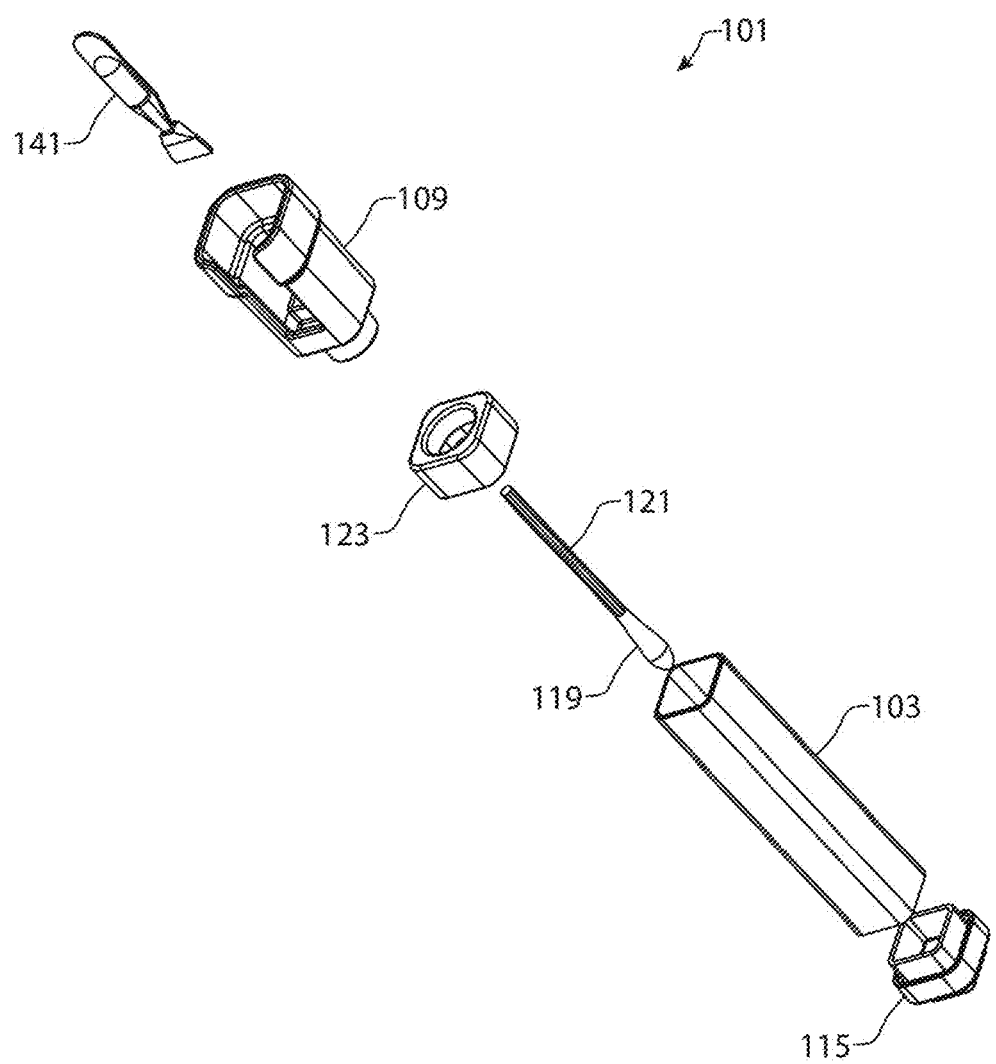
FIGS. 6-10 are exploded views of the swab canister of FIG. 3.
Figure 7:
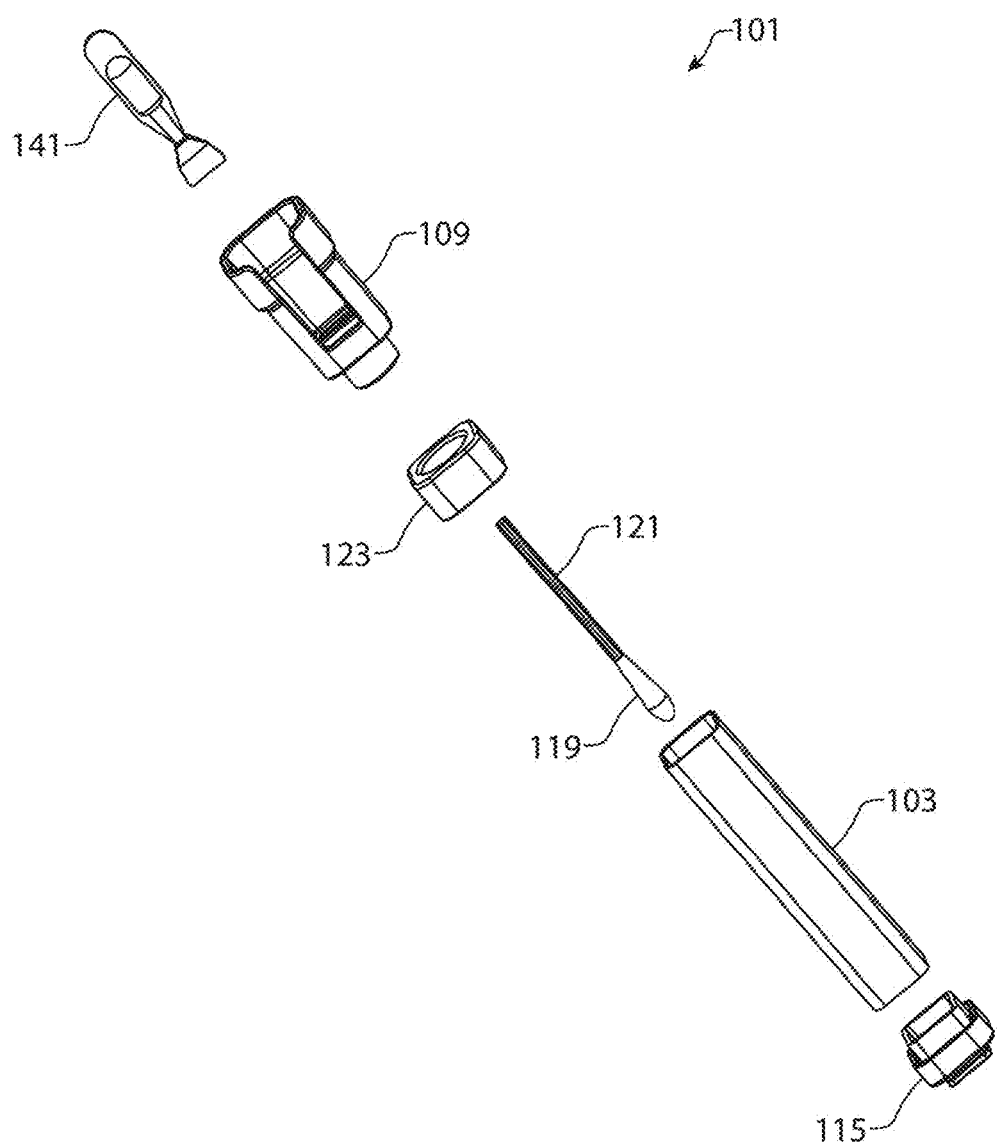
Figure 8:
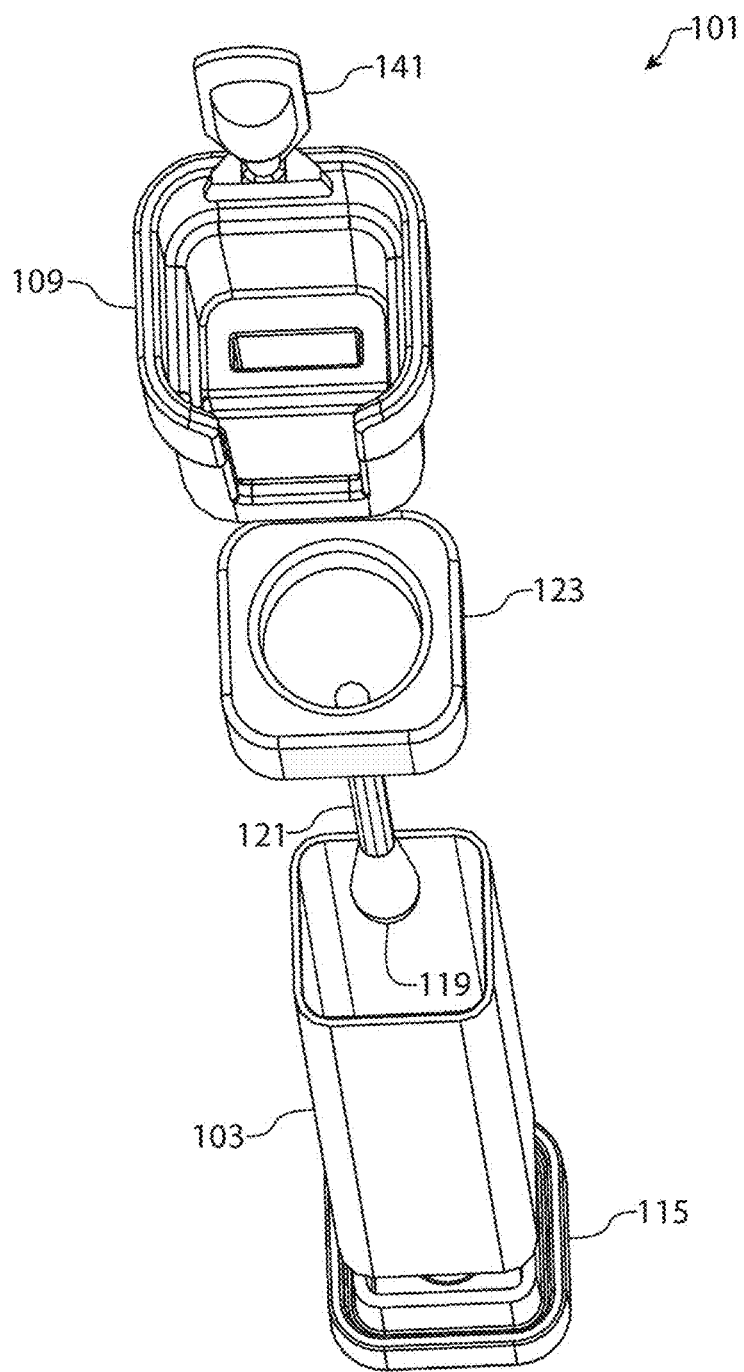
Figure 9:
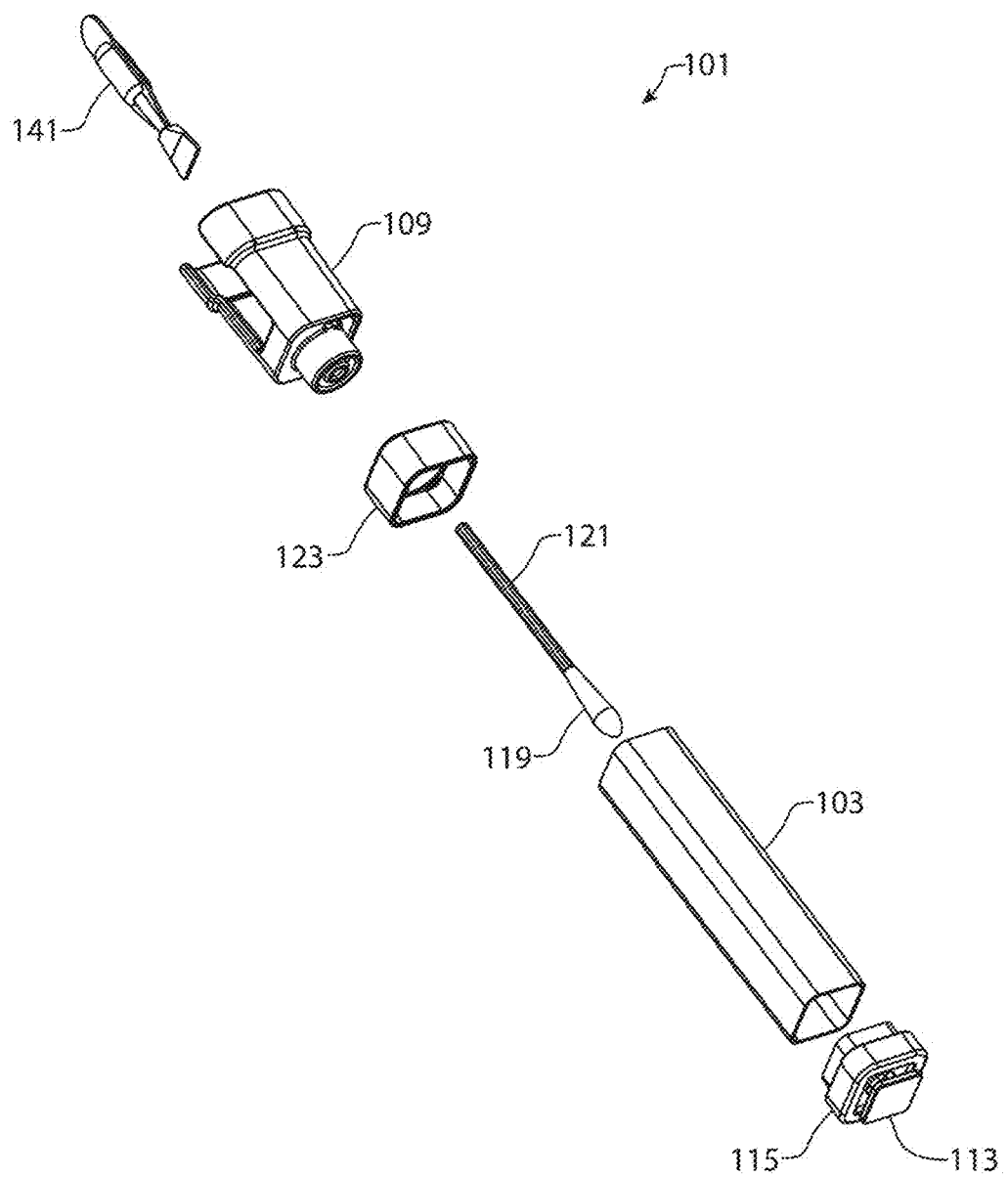
Figure 10:
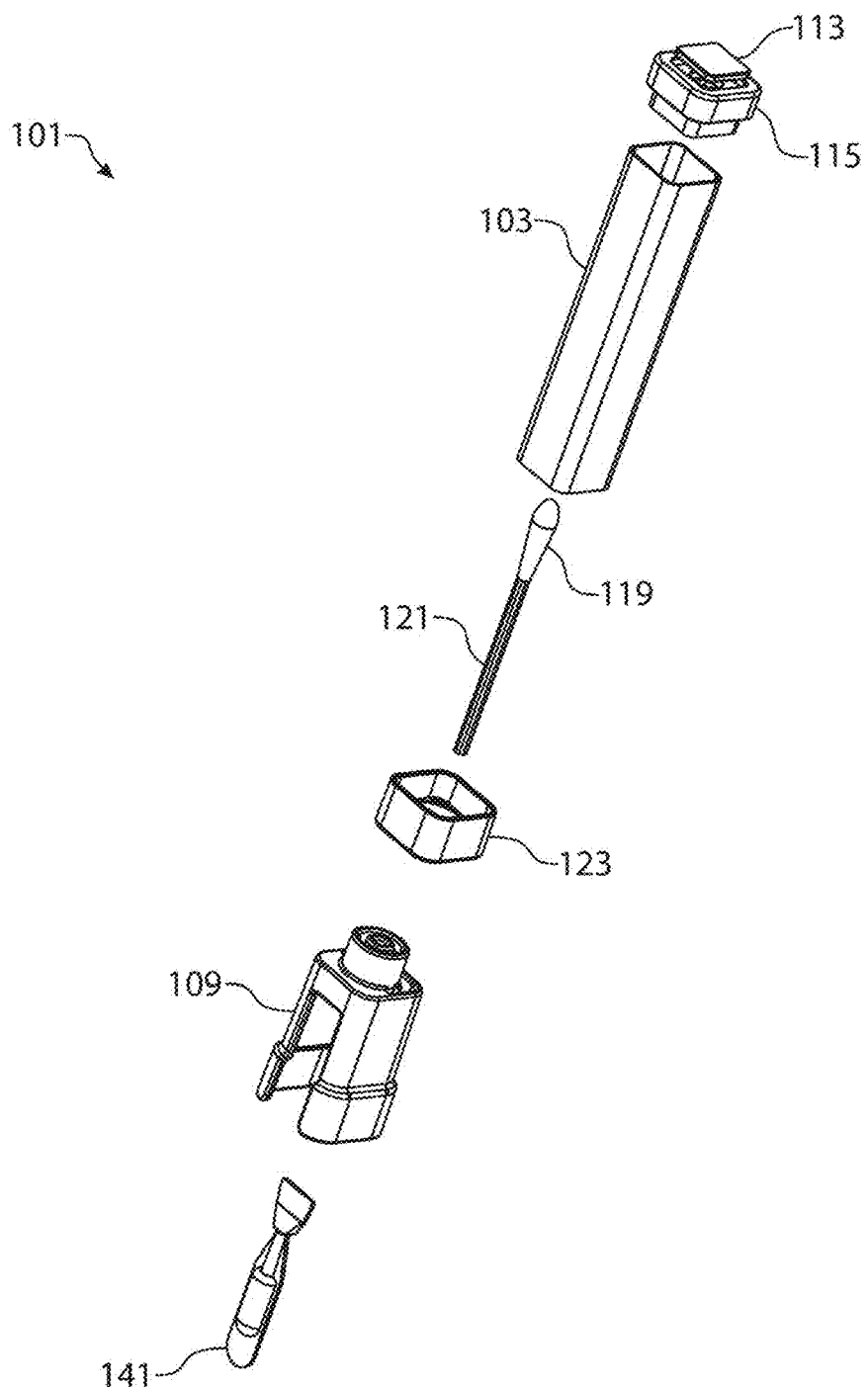
Figure 11:
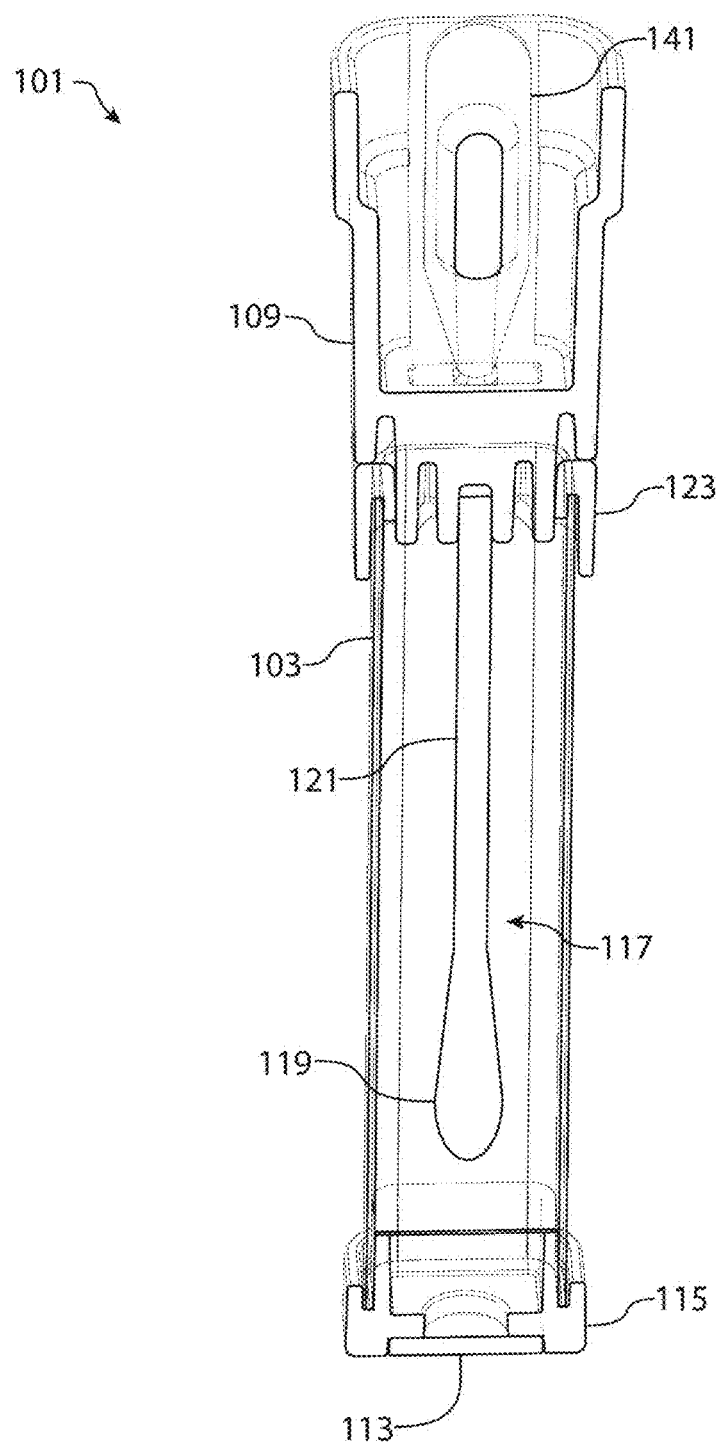
FIG. 11 is a cross-sectional view taken along LINE 11-11 of FIG. 3.
Figure 12:
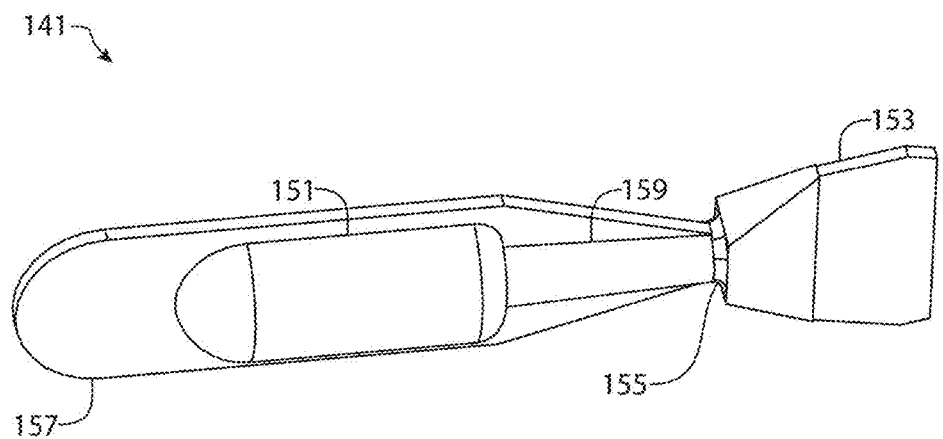
FIGS. 12-15 are perspective views of the ampule of the swab canister of FIG. 3.
Figure 13:
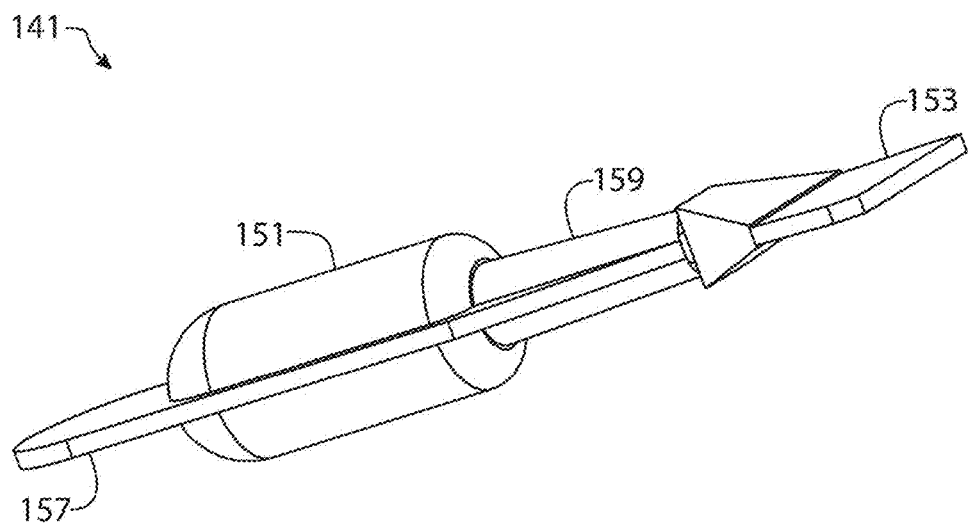
Figure 14:
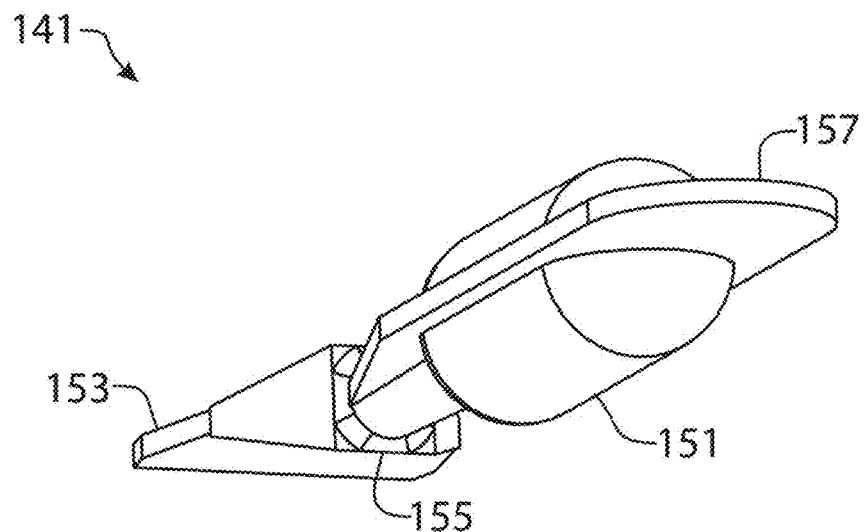
Figure 15:
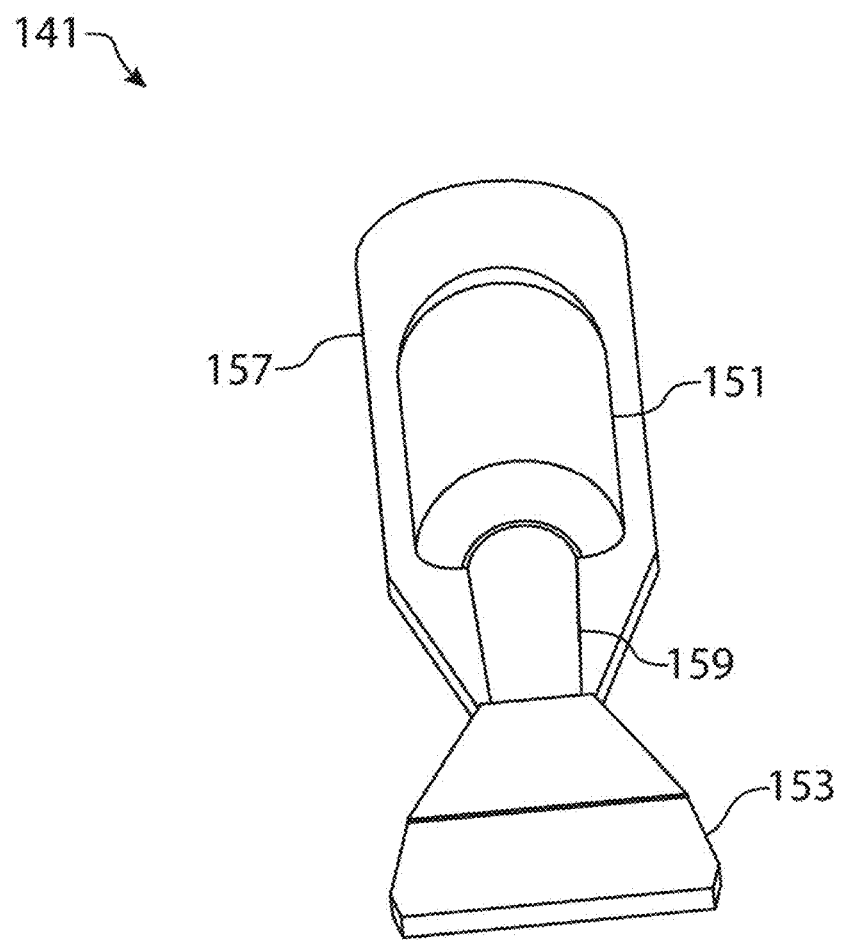
Figure 16:
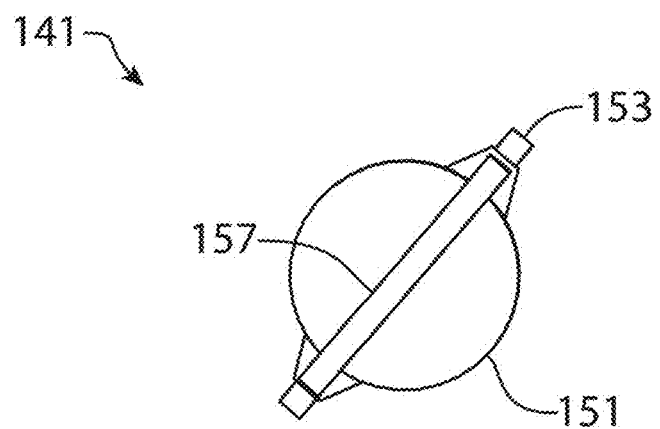
FIG. 16 is a top view of the ampule of FIG. 3.
Figure 17:
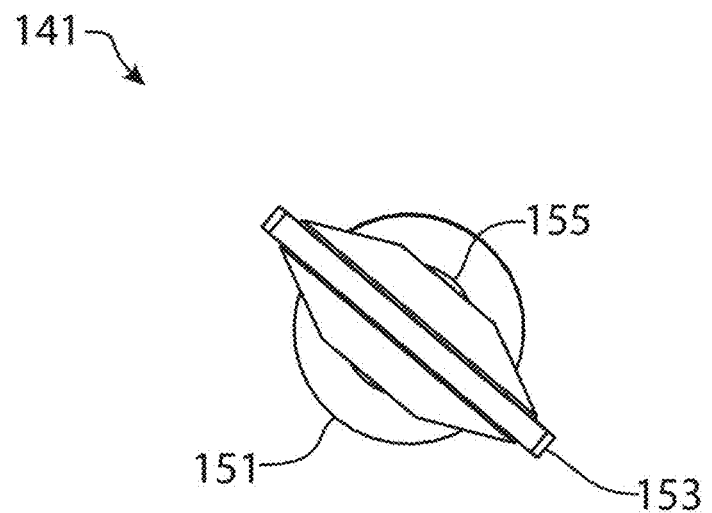
FIG. 17 is a bottom view of the ampule of FIG. 3.
Figure 18:
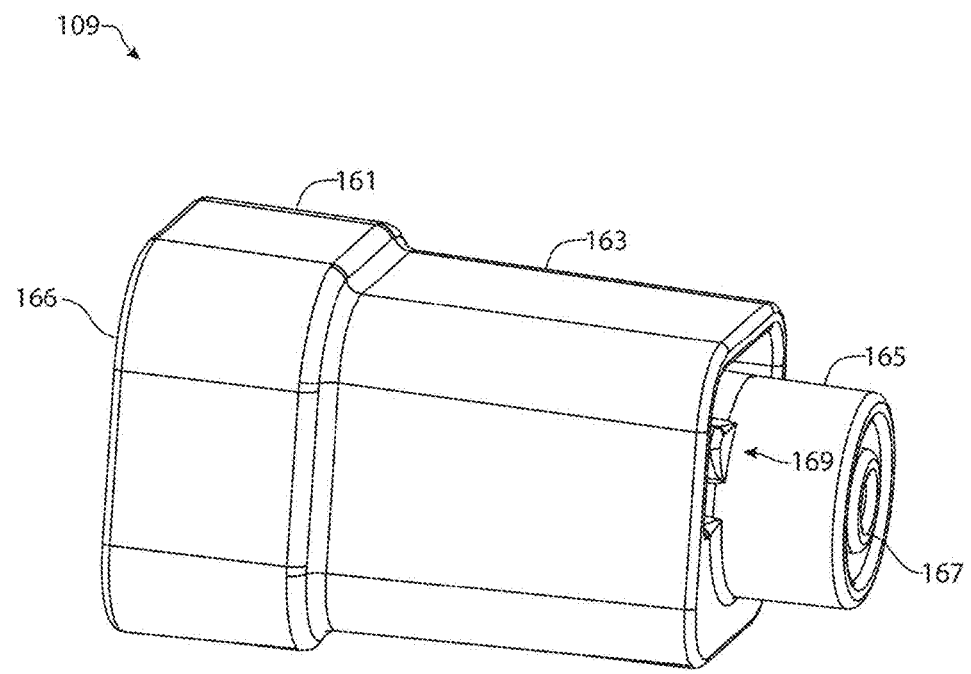
FIG. 18 is a perspective view of the second cap of the swab canister of FIG. 3.
Figure 19:
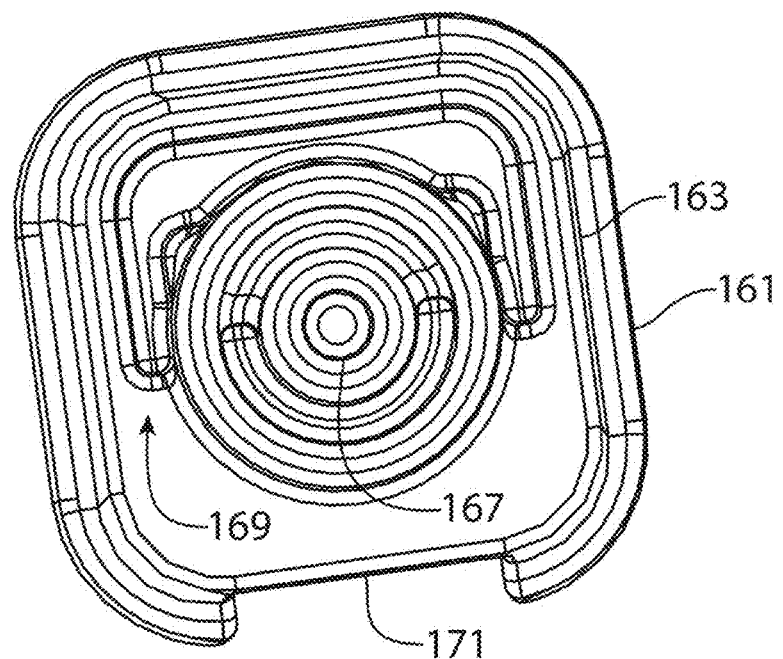
FIG. 19 is a bottom view of the second cap of the swab canister of FIG. 3.
Figure 20:
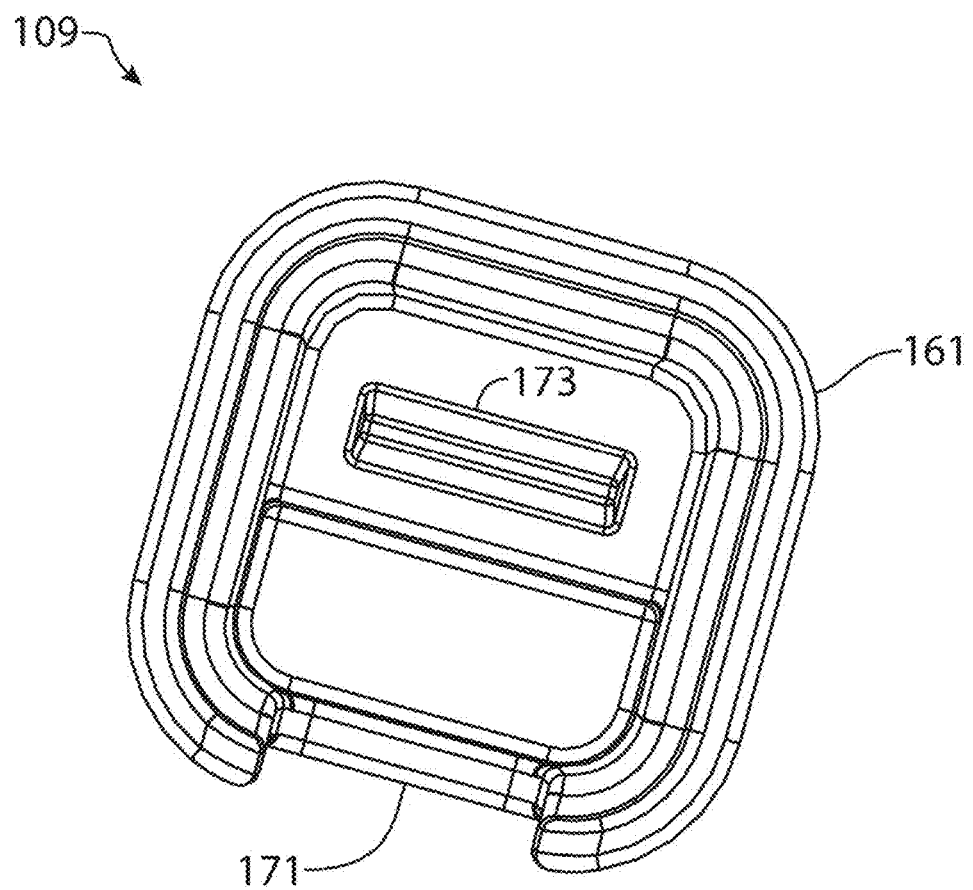
FIG. 20 is a top view of the second cap of the swab canister of FIG. 3.
Figure 21:
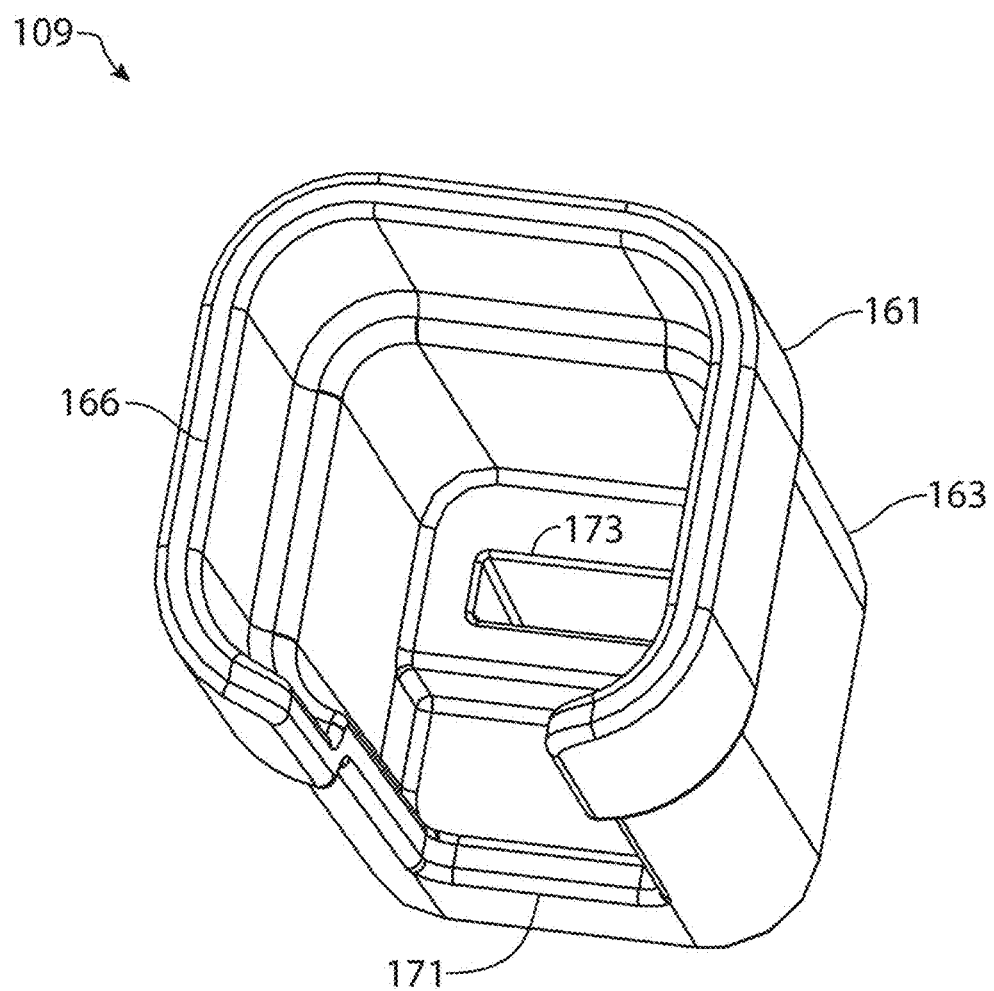
FIGS. 21-25 are perspective views of the second cap of the swab canister of FIG. 3.
Figure 22:
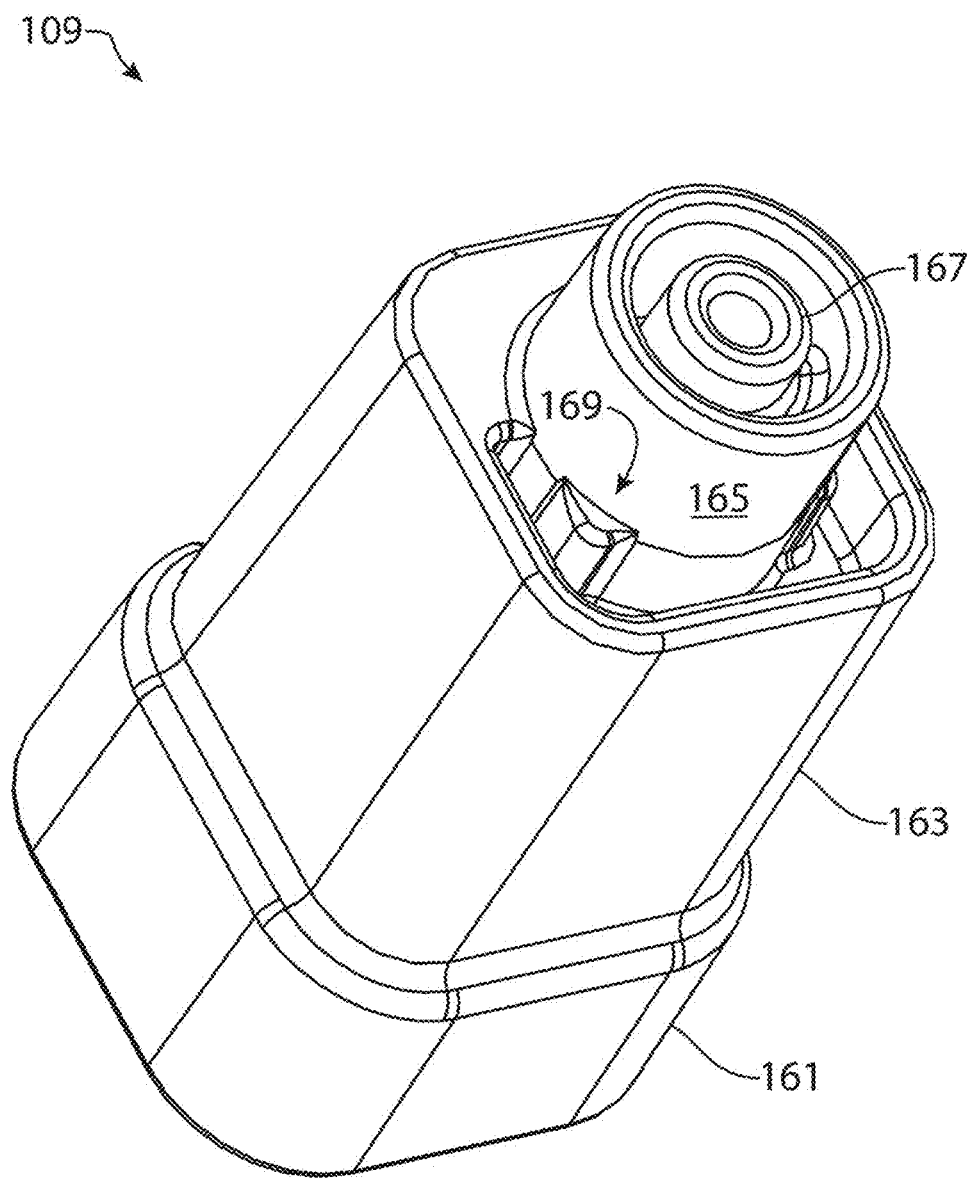
Figure 23:
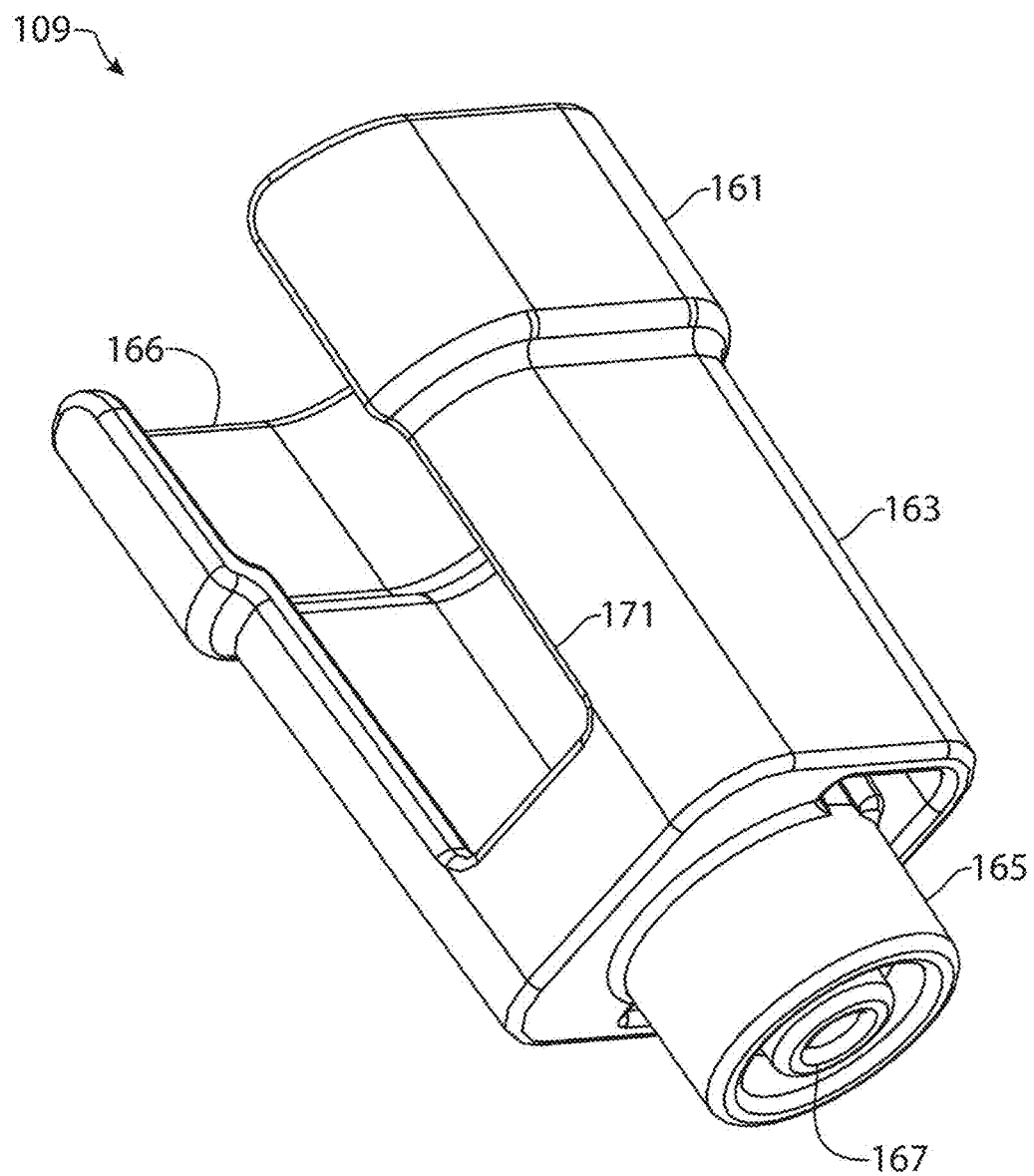
Figure 24:
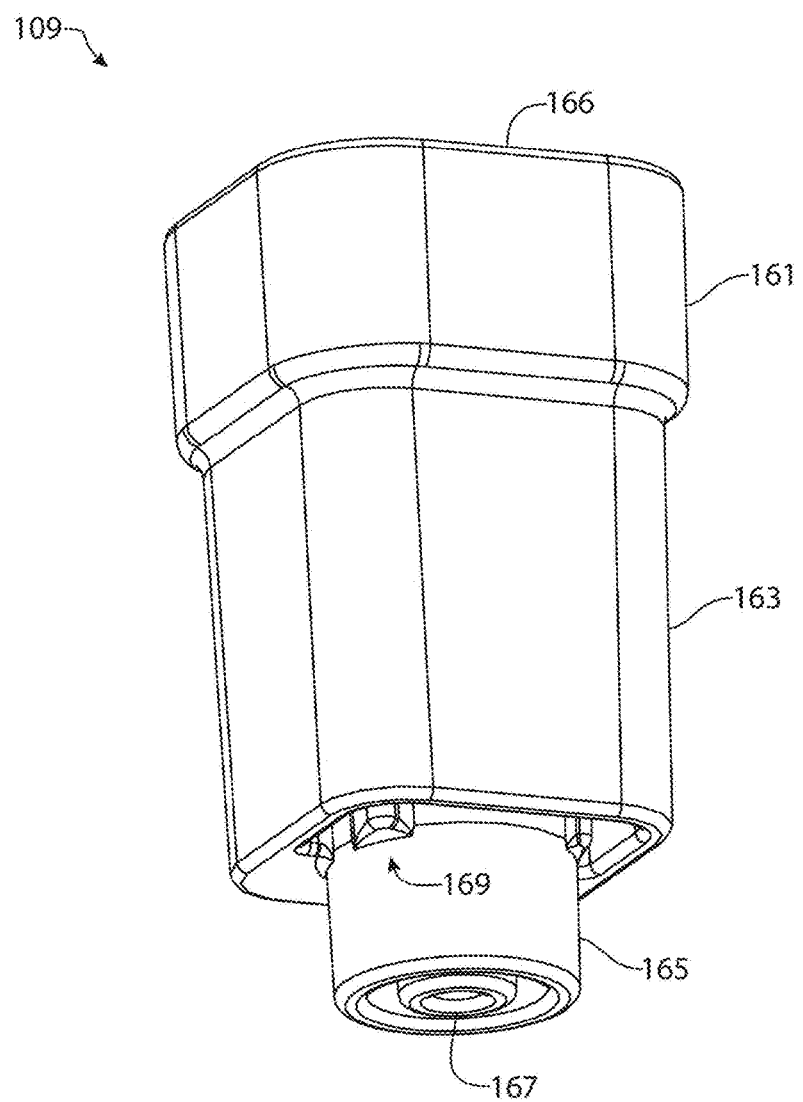
Figure 25:
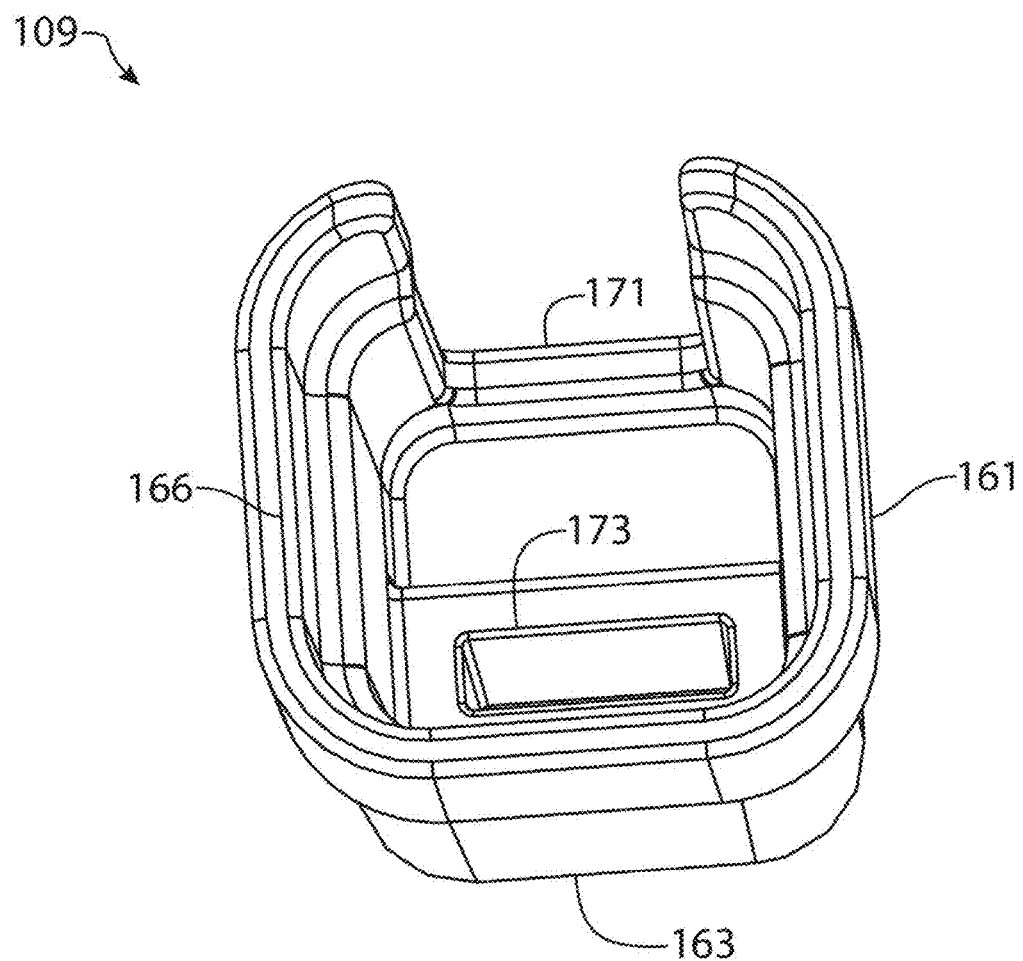
Figure 26:
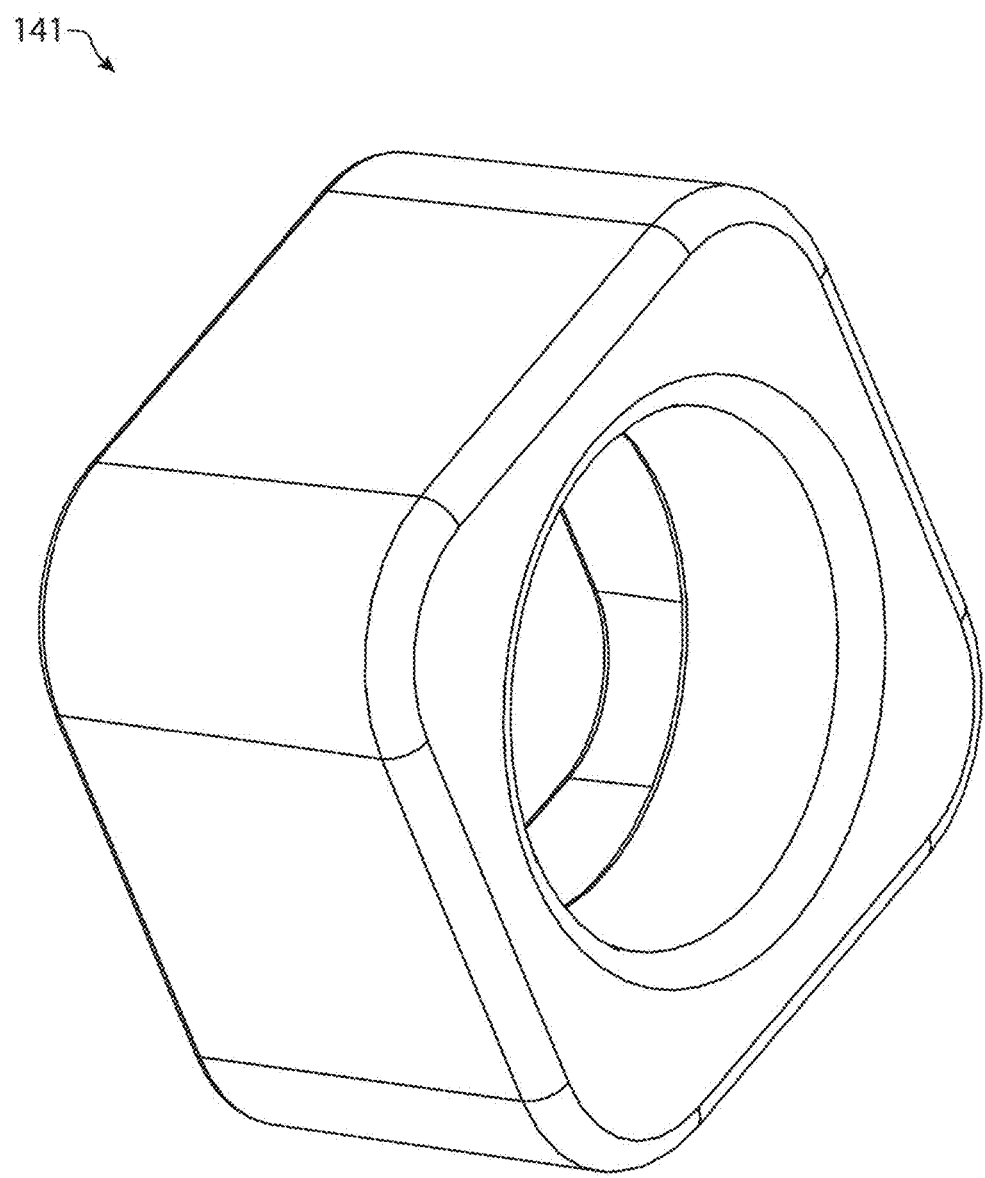
FIGS. 26-27 are perspective views of the adapter of the swab canister of FIG. 3.
Figure 27:
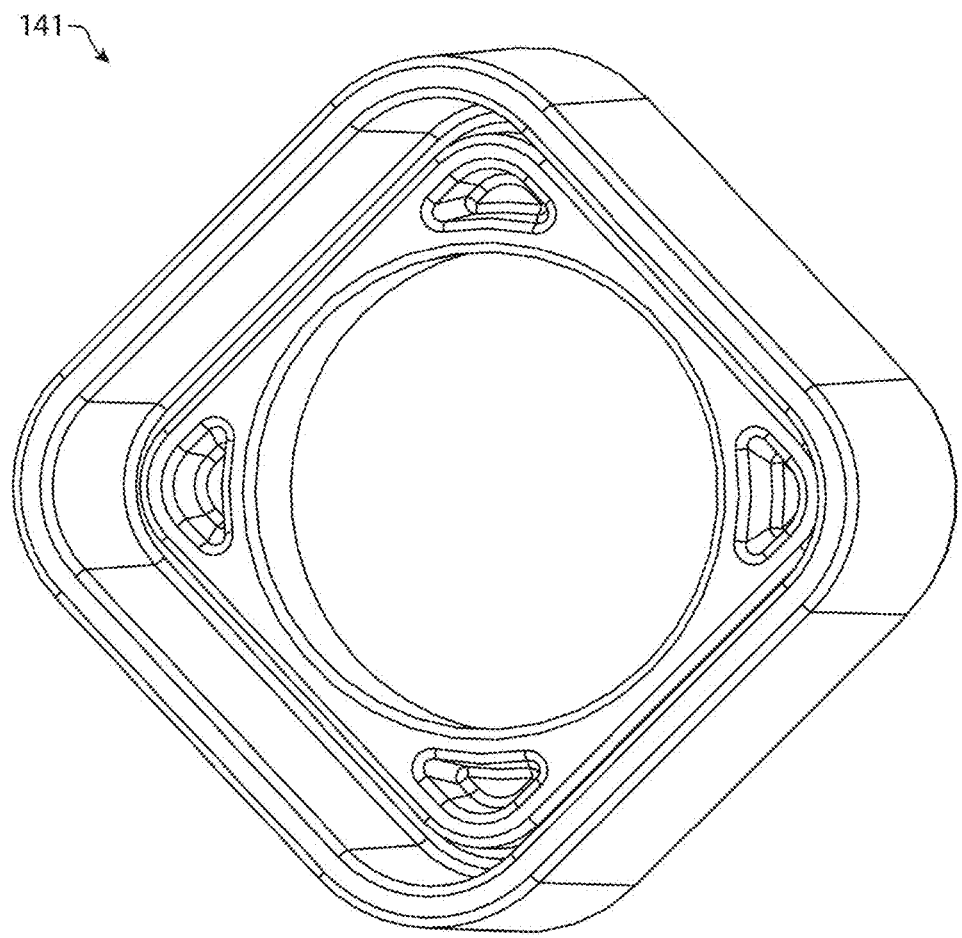
Figure 28:
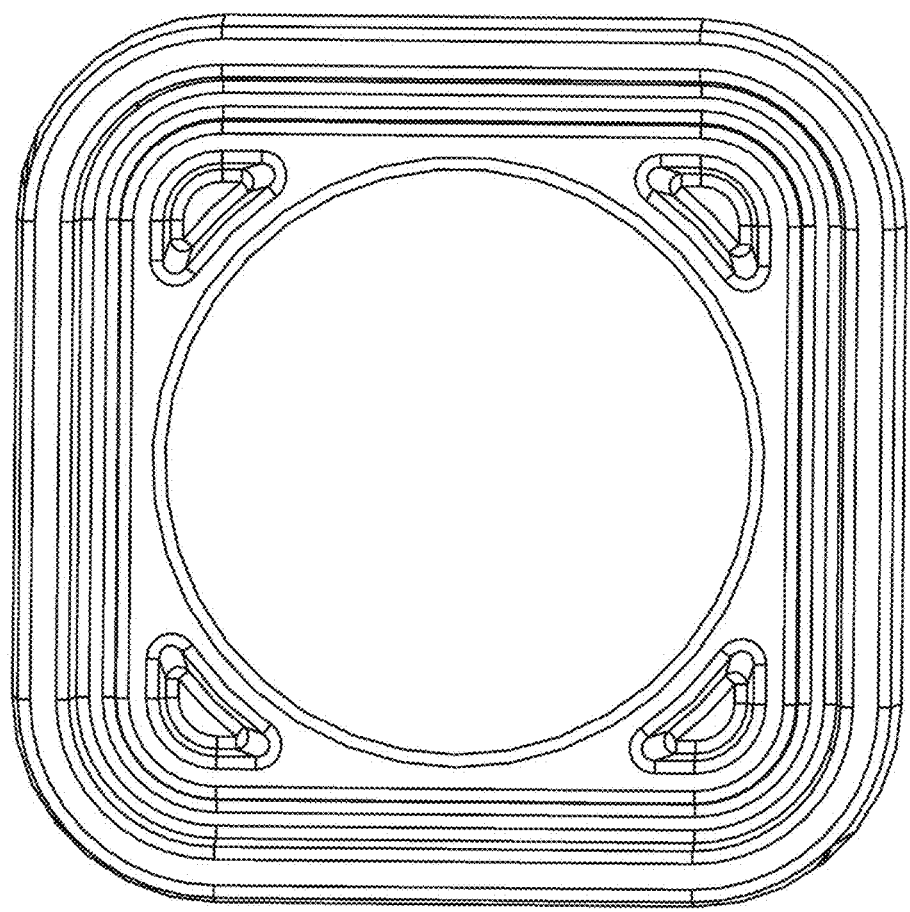
FIG. 28 is a top view of the adapter of the swab canister of FIG. 3.
Figure 29:
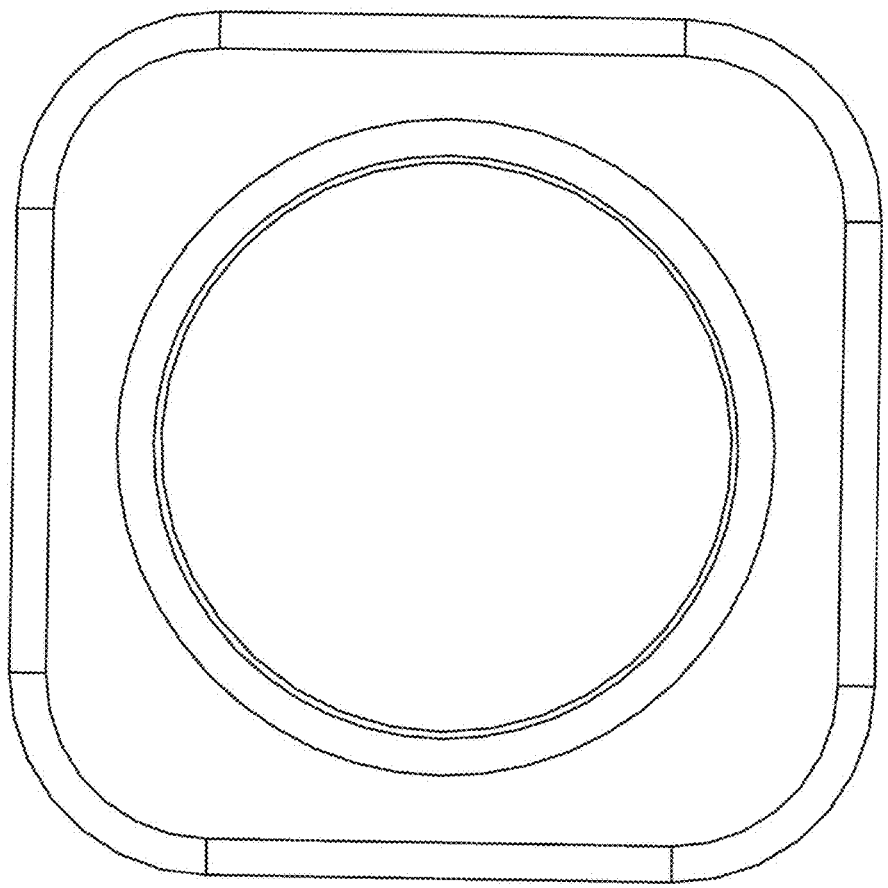
FIG. 29 is a bottom view of the adapter of the swab canister of FIG. 3.
Figure 30:
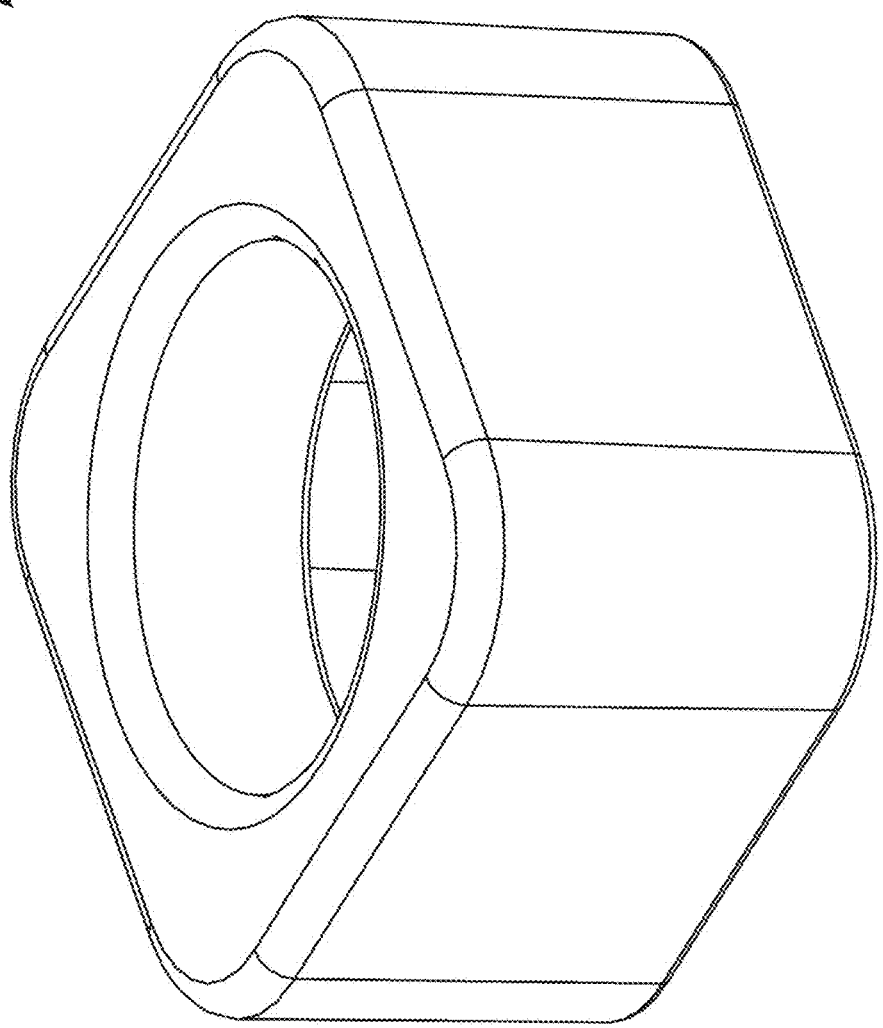
FIG. 30 is a perspective view of the adapter of the swab canister of FIG. 3.
Figure 31:
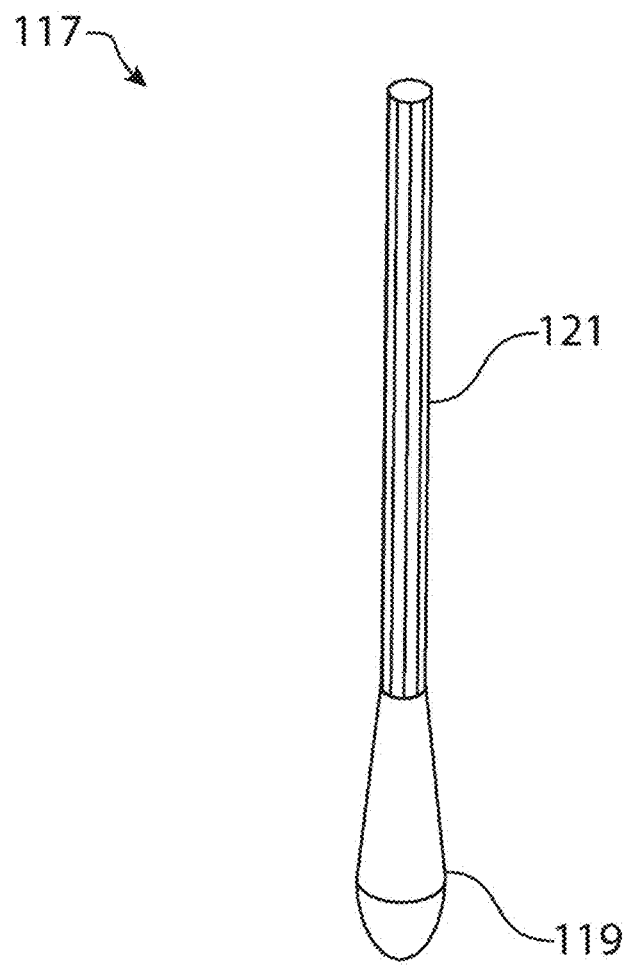
FIG. 31 is a perspective view of the sample collector of the swab canister of FIG. 3.

While the prior art swab canister depicted in FIGS. 1-2 may have some desirable features, it also suffers from some notable infirmities. In particular, this sample canister is not readily amenable to treatment with ethylene oxide, since ethylene oxide cannot be utilized in the presence of common desiccants such as silica. While the packets of desiccant in the swab canister of FIGS. 1-2 could ostensibly be added after treatment of the swab canister with ethylene oxide, doing so would defeat the purpose of that treatment, since the interior of the swab canister would then be exposed to potential contaminants during desiccant placement. There is thus a need in the art for a sample swab canister which overcomes the aforementioned issues.

It has now been found that the foregoing needs may be met with the devices and associated methodologies which are described herein. In a preferred embodiment, a sample swab canister is disclosed in which the interior of the canister is sealed from the external environment by way of a membrane that is permeable to moisture and a (preferably gaseous) sanitizing agent (such as, for example, ethylene oxide). The membrane thus allows the interior of the canister to be treated post-manufacture to sterilize it and to destroy the DNA footprint of any biological materials present therein, while also sealing off the interior of the canister from environmental contaminants. Since the membrane is moisture permeable, a suitable desiccant can be positioned externally to (and preferably proximal to) the membrane after the swab canister has been sanitized as, for example, by placing it in a cap which is positioned over the external surface of the membrane. This approach permits the removal of moisture content from collected samples, while avoiding any interaction between the sanitizing agent and the desiccant. This approach also avoids the introduction of contaminants during placement of the desiccant.

Figure 32:
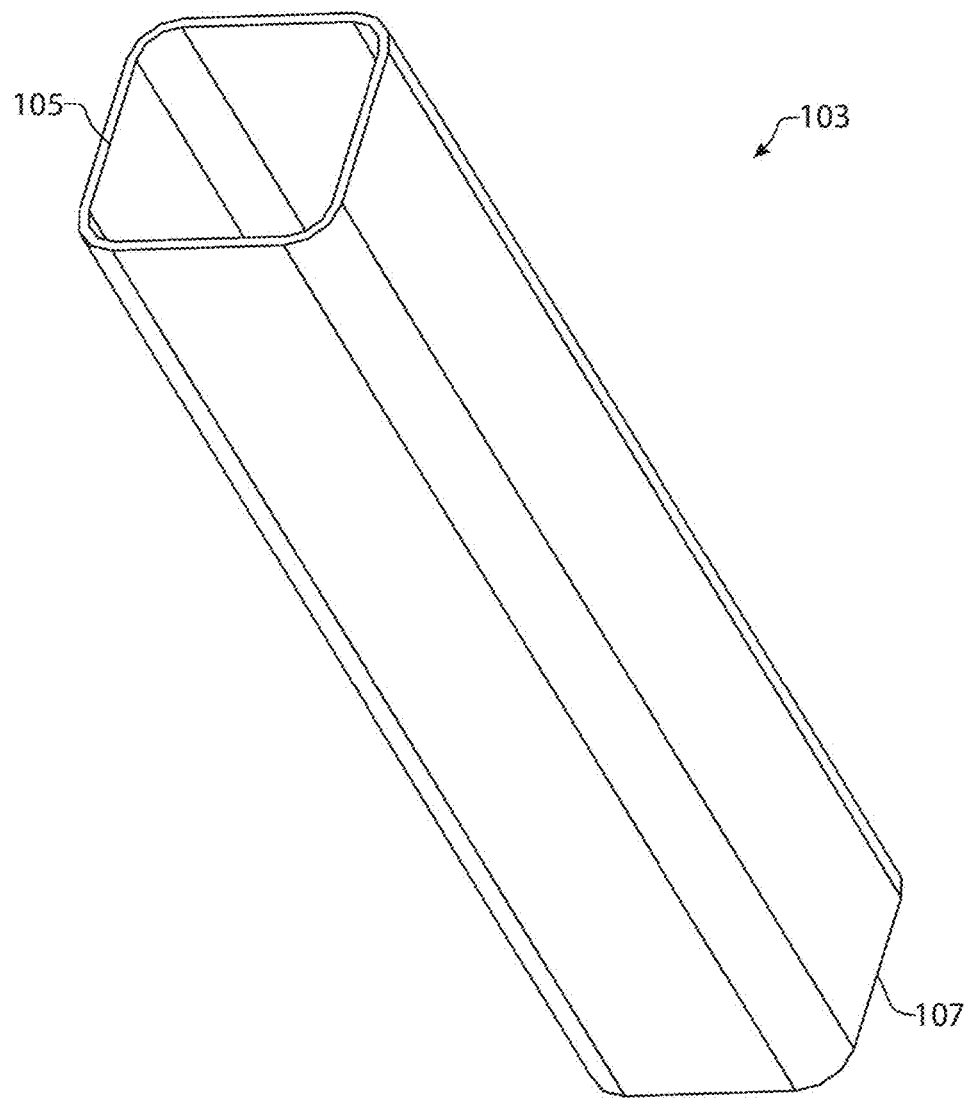
FIGS. 32-33 are perspective views of the container of the swab canister of FIG. 3.
Figure 33:
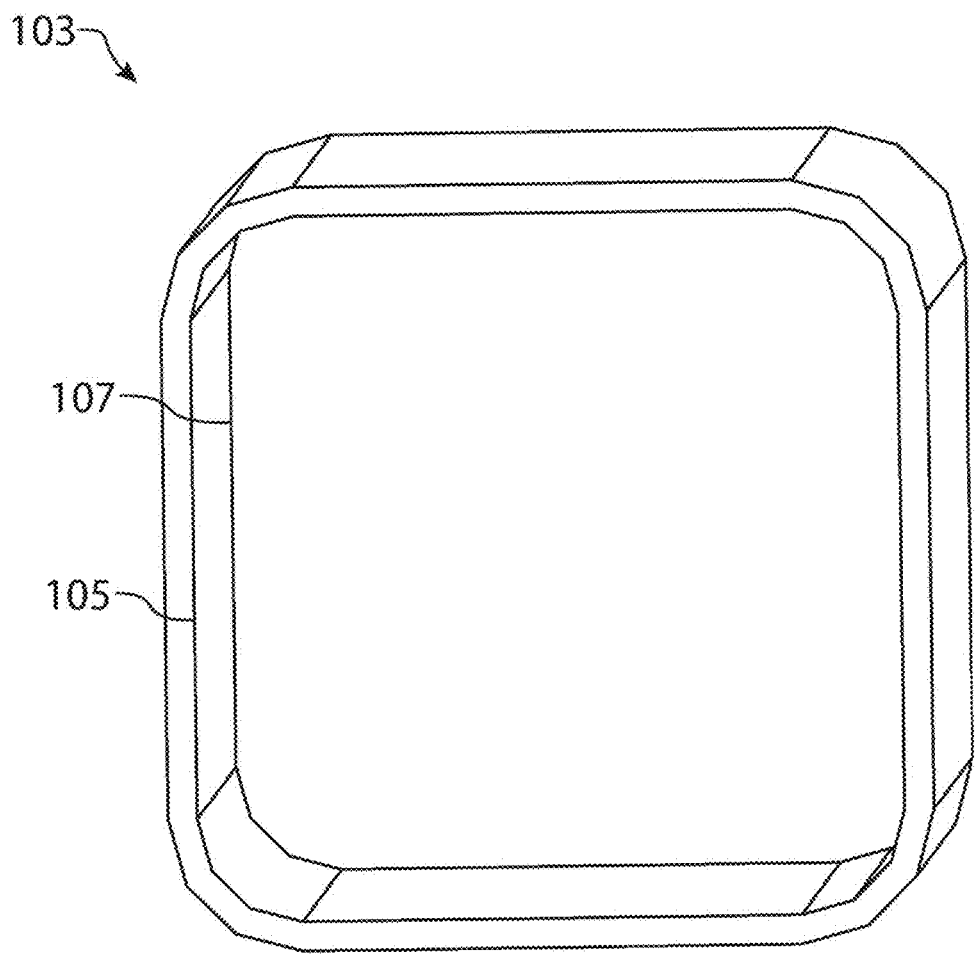
Figure 34:
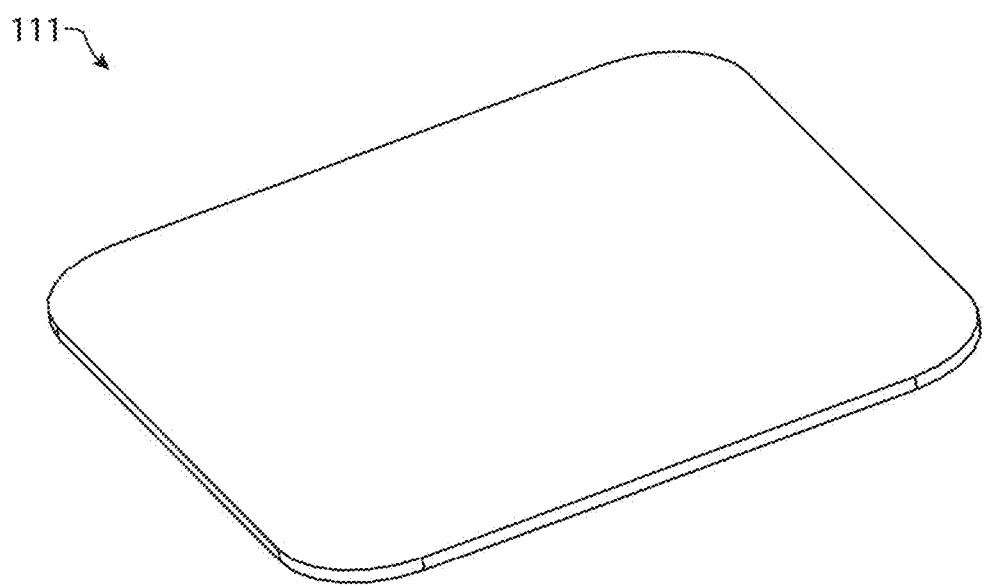
FIG. 34 is a perspective view of the membrane of the swab canister of FIG. 3.
Figure 35:
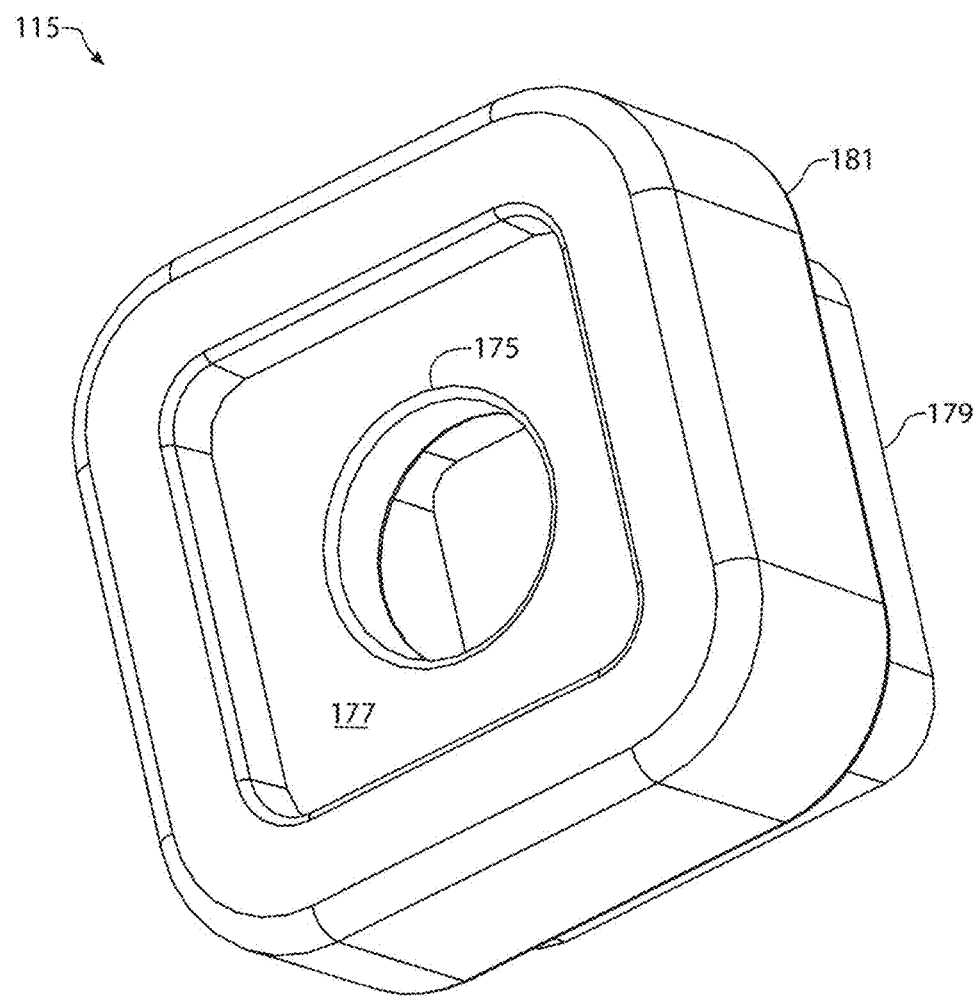
FIGS. 35-37 are perspective views of the first cap of the swab canister of FIG. 3.
Figure 36:
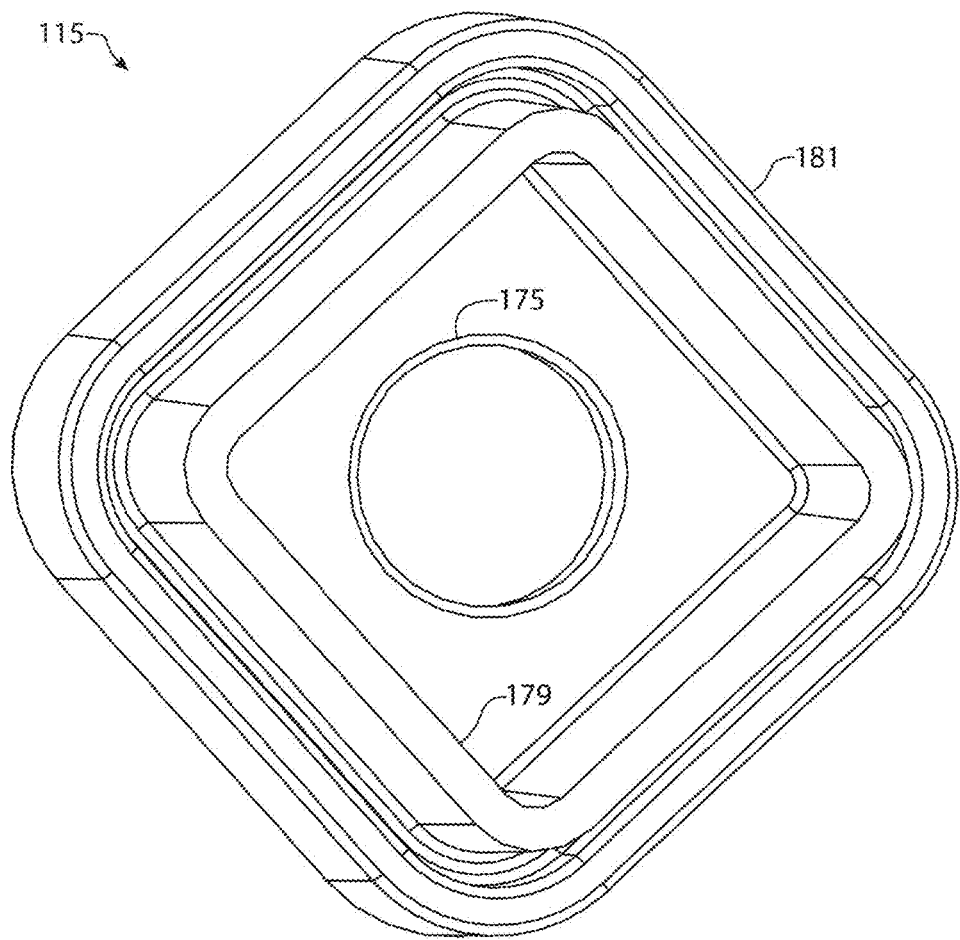
Figure 37:
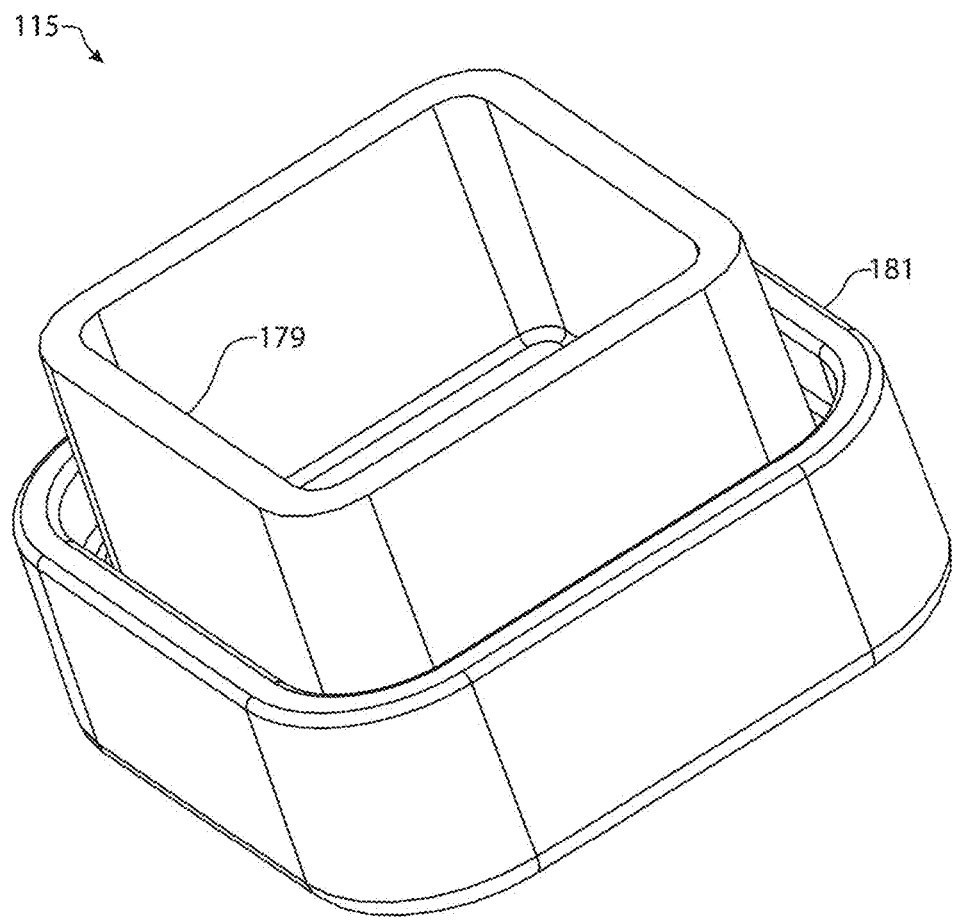
Figure 38:
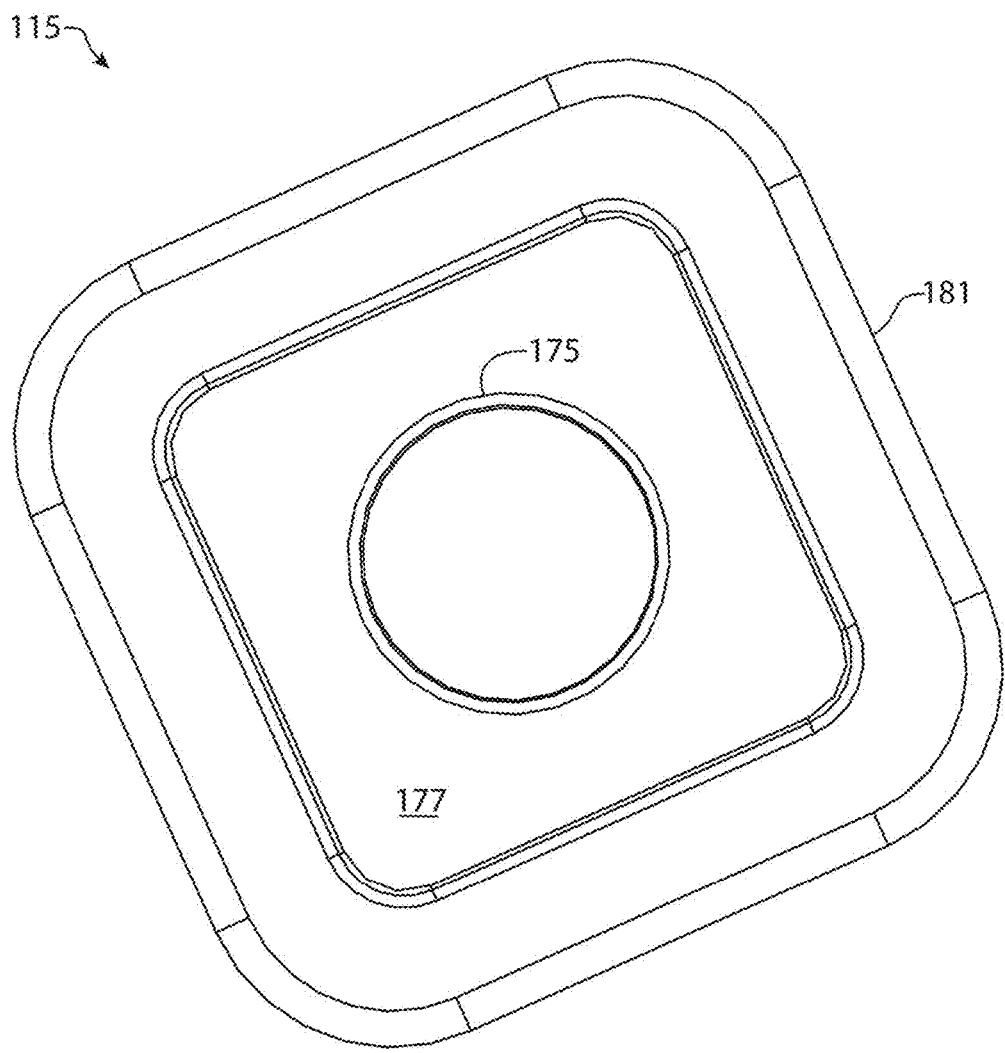
FIG. 38 is a top view of the first cap of the swab canister of FIG. 3.
Figure 39:
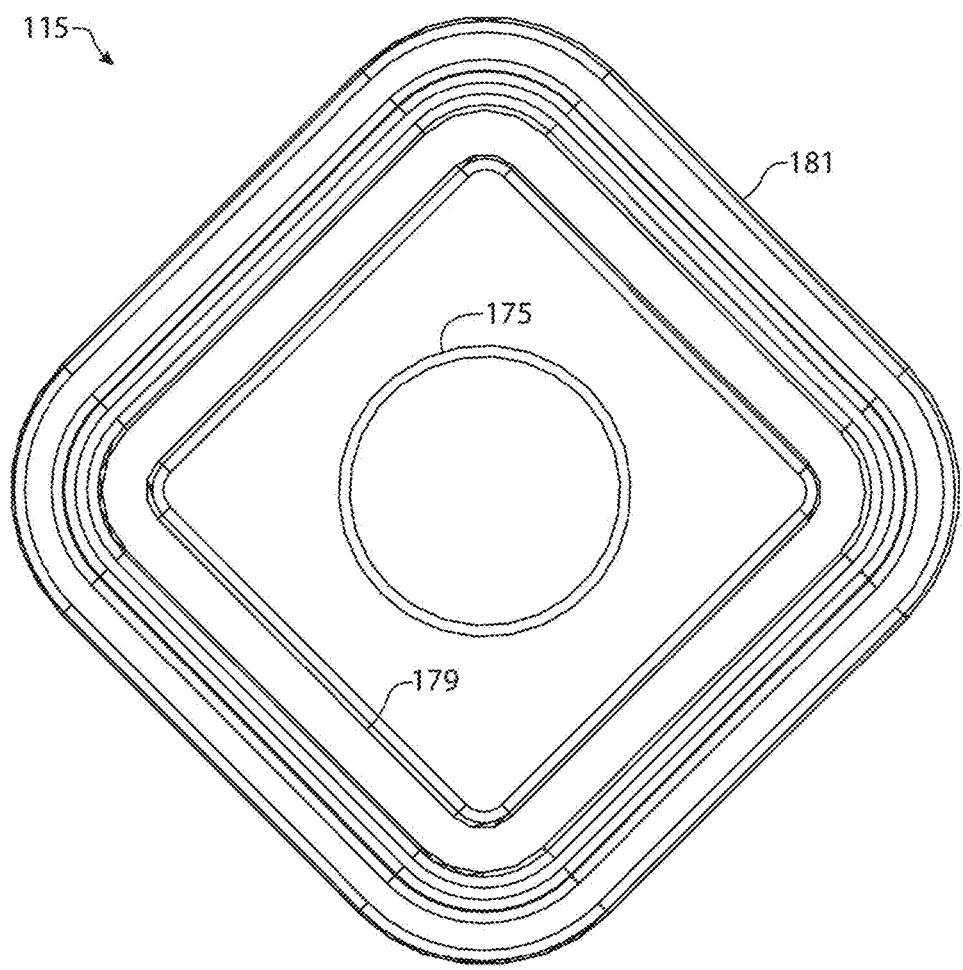
FIG. 39 is a bottom view of the first cap of the swab canister of FIG. 3.

FIGS. 3-43 depict a first particular, non-limiting embodiment of a swab canister 101 in accordance with the teachings herein. With reference to FIGS. 3-11, the swab canister 101 in this particular embodiment includes a container 103 which is parallelepiped in shape and which is essentially rectangular in a cross-section taken in a plane parallel to its longitudinal axis. This shape is advantageous in that it contains multiple flat faces which prevent the swab canister 101 from rolling when it is placed on a sloped surface, and which provide areas on which sample identification tags may be affixed or notations may be written (e.g., with a permanent marker). As best seen in FIGS. 32-33, the container 103 has first 105 and second 107 openings on first and second opposing ends thereof, respectively.

With reference to FIGS. 3-11, the first opening 107 in the container 103 has a first cap 115 disposed therein. The first cap 115, which is shown in greater detail in FIGS. 35-39, is equipped with a central depression 177 and a central apertures 175 on a first surface thereof. The first cap 115 is further equipped with first 179 and second 181 outer surfaces. The first outer surface 179 is indented with respect to the second outer surface 181 to allow the first cap 115 to be mounted onto the container 103.

The first cap 115 may be removable or may be permanently fixed in place, and is equipped with a membrane 111 (see FIG. 34) that is permeable to both moisture and to ethylene oxide. This membrane 111 may comprise, for example, flash-spun high density polyethylene fibers such as those sold under the tradename Tyvek® by E. I. do Pont de Nemours, Inc. (Wilmington, Del.). The first cap 115 has an interior volume which may be utilized to house a suitable desiccant, which may be in solid, powder, or granular form. The desiccant may be housed in one or more packets, which may be inserted into the first cap 115. The first cap 115 may be equipped with surface features on its interior (such as, for example, protrusions, indentations or rails) to hold the desiccant 113 (or packets thereof) in place.

In some embodiments, the first cap 115 may be assembled from two or more components. In such embodiments, a first component of the first cap 115 may contain the membrane 111 and may be utilized to seal the container 103 such that a first surface of the membrane 111 is in fluidic communication with the external environment, and a second surface of the membrane 111 is in fluidic communication with the interior of the container 103. The interior of the container may then be sanitized or treated by passing ethylene oxide (or another suitable sanitizing agent) through the membrane 111, after which a second component of the first cap 115 may be attached to the first component to completely seal off the interior of the container 103 from the external environment. For example, the second component of the first cap 115 may releasably or permanently engage the first component of the first cap 115 through suitable threading, prongs, fasteners, or adhesives. The second component of the first cap 115 may have the desiccant seated therein.

It will be appreciated that the foregoing approach, and the two-part construction of the first cap 115 which may be utilized to implement it, help to ensure that the sterility of the interior of the container 103 is maintained throughout the assembly process, and that any contaminants introduced during manufacture (including those that might otherwise act as spurious sources of DNA) are sufficiently degraded and rendered inactive. It will also be appreciated that this approach prevents the desiccant from interfering with the sanitization process, since the desiccant is introduced (without the possibility for contamination) at a later point in the process.

The sample canister 101 further comprises a second cap 109 which is disposed on an opposing end 105 of the container 103 from said first cap 115. The second cap 109, which is depicted in FIGS. 18-25, has a sample collector 117 (shown in greater detail in FIG. 31) disposed thereon which, in the embodiment depicted, comprises a portion of an absorbent material 119 such as cotton disposed on a stem 121. Preferably, the sample collector 117 is a cotton swab similar to the type currently sold under the brand name Q-tips™, and is connected on one end thereof the to the second cap 109. In some embodiments, the sample collector 117 may be equipped with a frangible joint which may be positioned, for example, along the length of the stem 121 or at the interface between the stem 121 and the second cap 109, so that the sample collector 117 (or a portion thereof) may be removed from the second cap 109.

The second cap 109 has a first segment 163 and second segment 161 which are dimensioned to allow the first segment 163 to be inserted into the adapter 123 (shown in greater detail in FIGS. 26-30) when the sample canister is not in use, and to allow the second segment to be placed over the adapter 123 when the sample canister is being used to collect a sample. The second cap 109 is equipped with an opening 166 and a sample collector holder 167 on opposing ends thereof, and is further equipped with features 169 to support the second cap 109 on the adapter 123.

Referring again to FIGS. 3-11, in the particular embodiment depicted, the second cap 109 is further equipped with an ampule 141 of fluid, such as deionized water or saline solution. The second cap 109 is appropriately dimensioned to house the ampule 141. The fluid within the ampule 141 is preferably sterilized and purified, and may be utilized during sample collection in situations where, for example, a liquid medium is required to dissolve or suspend a portion of sample material (such as, for example, dried blood) to enable or facilitate sample collection.

As seen in FIGS. 12-17, the ampule 141 is equipped with a central reservoir 151 that holds a portion of a liquid medium. The central reservoir 151 is in open communication with a conduit 159, the distal end of which is sealed off with a tab 153. The tab 153 is equipped with a flattened surface which is easy to grasp, and is adjoined to the conduit 159 by way of a frangible or tear-able seal 155. The opposing end of the ampule 141 from the tab 153 is equipped with a flattened surface 157. The flattened surface 157 on the body of the ampule and the flattened surface of the tab 153 allow the ampule to be readily grasped on each end so that the frangible seal 155 may be easily broken. This construction allows the ampule to be readily opened in the field when use of the fluid is required.

Figure 40:
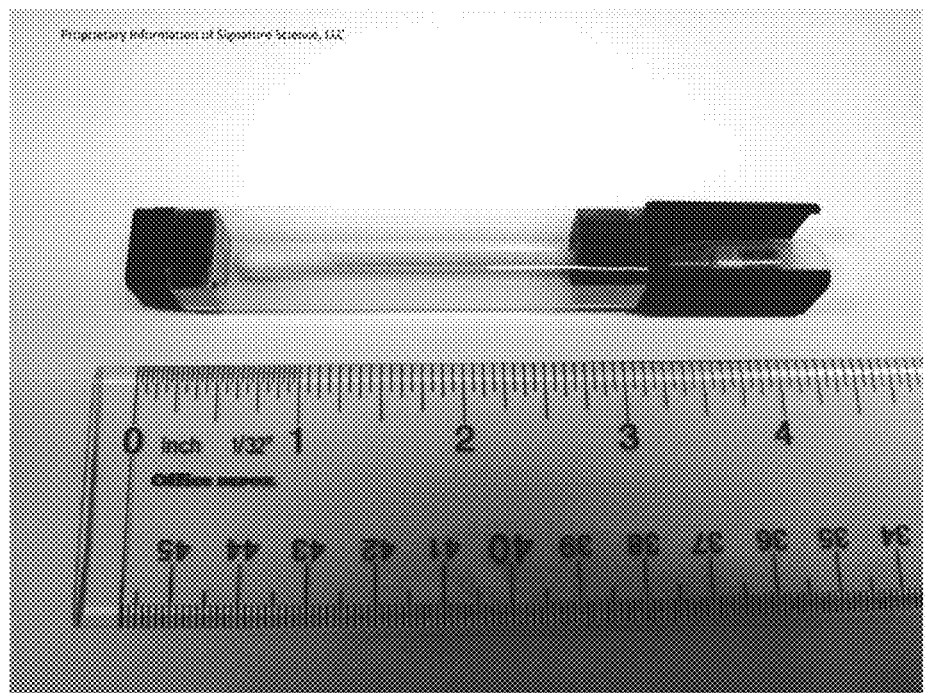
FIG. 40 is a perspective view of the swab canister of FIG. 3, showing the canister prior to use and in a closed configuration. The canister is accompanied by a ruler to show the dimensions of the canister.
Figure 42:
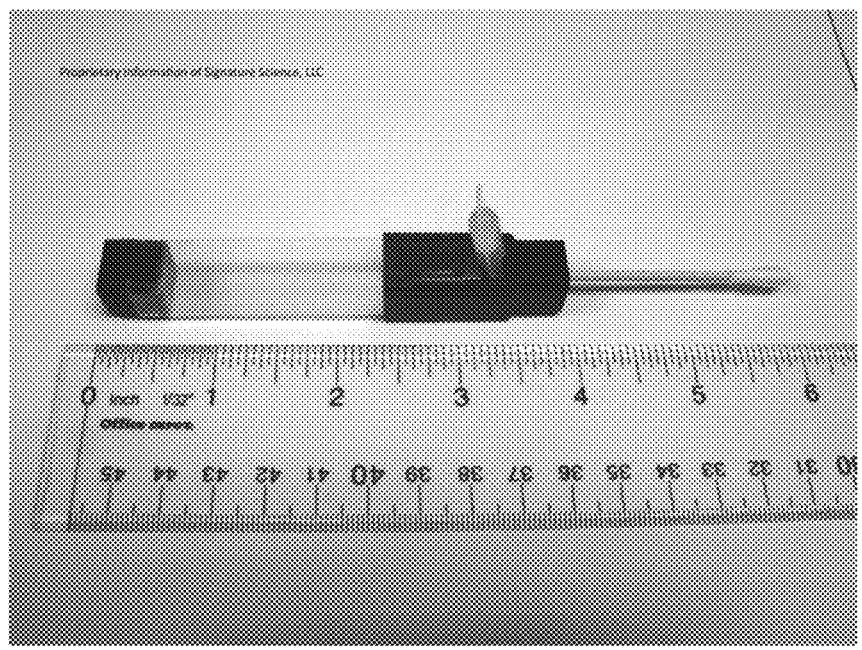
FIGS. 42-43 are perspective views of a swab canister similar to that of FIG. 3, showing the canister ready for use and in an open configuration. The swab canister is accompanied by a ruler to show the dimensions of the canister. In the embodiment depicted, the end use requires the use of water for sampling purposes, so a water ampoule has been provided in the cap of the canister and is positioned so that it is ready to be twisted off.
Figure 43:
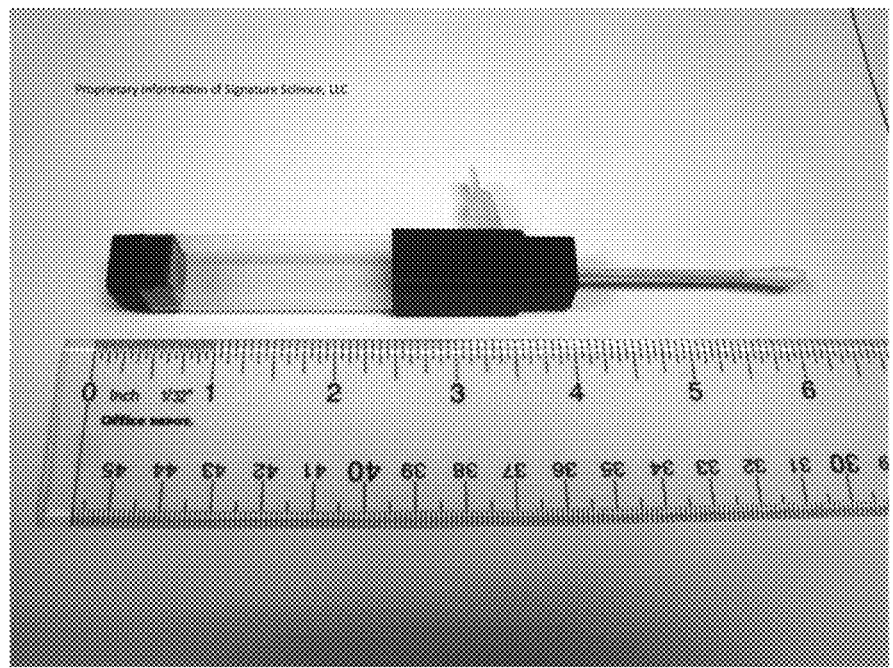
Figure 44:
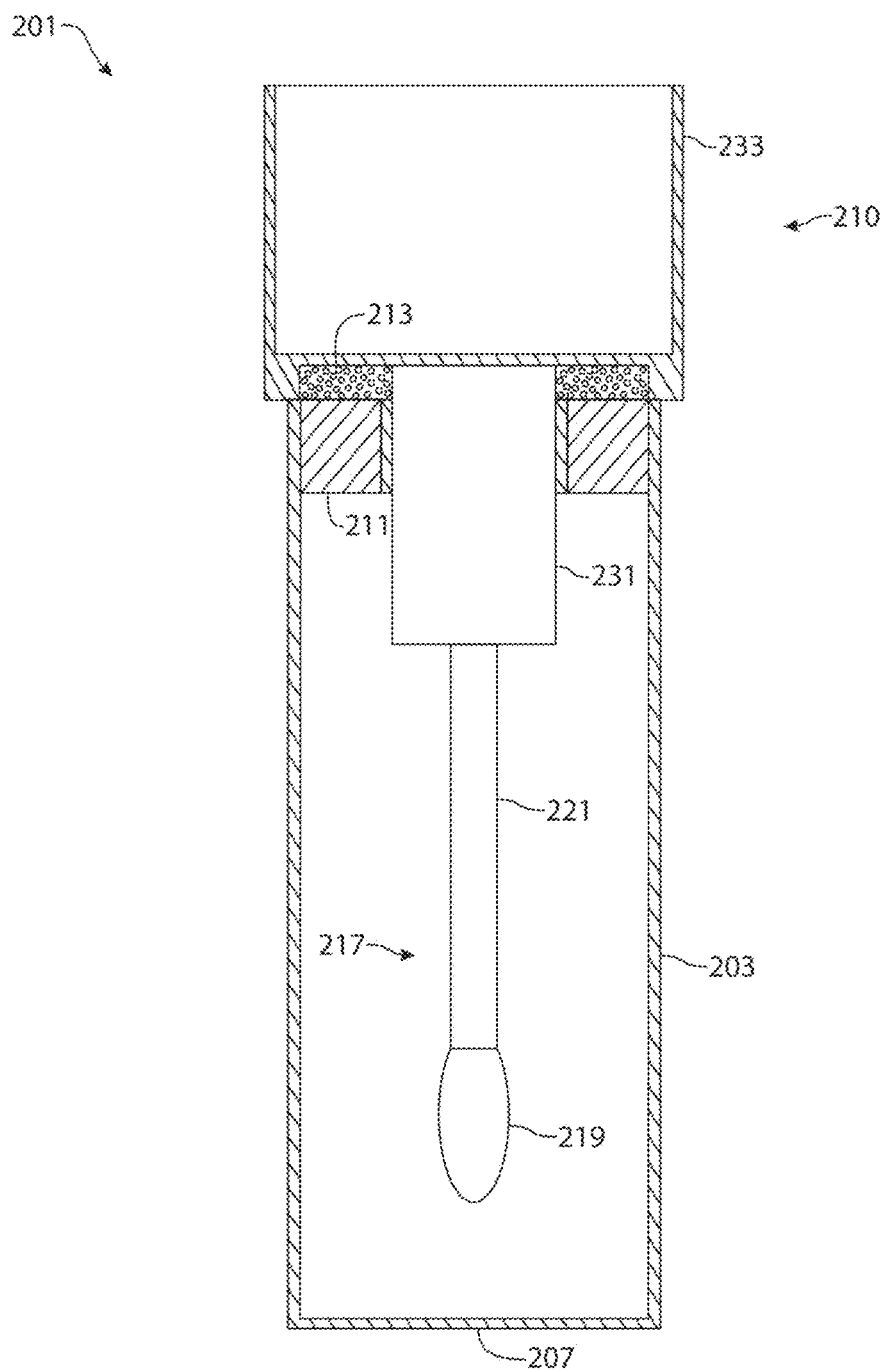
FIG. 44 is a perspective view of a second particular, non-limiting embodiment of a swab canister in accordance with the teachings herein, showing the canister in a closed configuration. In this embodiment, the desiccant, water permeable membrane and opening for the swab are all disposed on one side of the container.

As seen by comparing FIGS. 40 and 42, the ampule 141 is pivotable from a first orientation in which it lays protected within the second cap 109 (but is accessible by way of an opening 143 therein; see FIG. 40), and a second orientation in which is protrudes through the opening 143 in the second cap 109. As seen in FIG. 42, in the embodiment depicted, the frangible seal or edge may be broken by flipping the ampule 141 into an upright position within the second cap 109, and then twisting the ampule 141 about its longitudinal axis. In some variations of this embodiment, rupturing the frangible seal or edge merely enables removal of the ampule 141 from the second cap 109, and a separate cap or frangible seal is provided on the ampule for access to the liquid contained therein.

Figure 41:
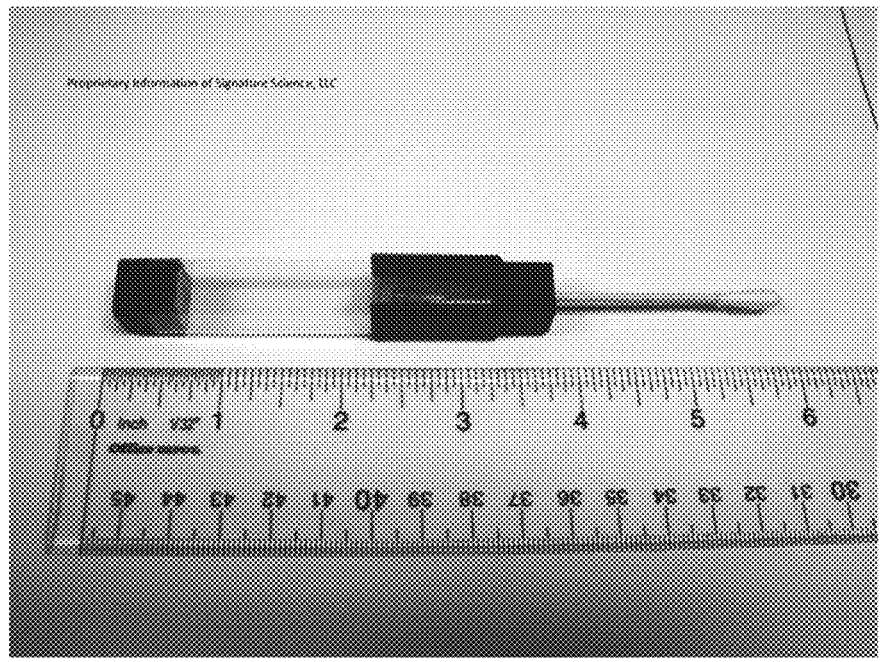
FIG. 41 is a perspective view of the swab canister of FIG. 3, showing the canister ready for use and in an open configuration. The swab canister is accompanied by a ruler to show the dimensions of the canister. In the embodiment depicted, the end use does not require the use of water for sampling purposes.

As will be appreciated by comparing FIG. 40 to FIG. 41, the swab canister 101 is transformable between a first configuration in which the sample collector 117 is housed in the container 103 and sealed off from the external environment, and a second orientation in which the sample collector 117 extends from the container 103. The swab canister 101 will typically be maintained in the second orientation during sample collection (and possibly during sample analysis), and will typically be maintained in the first orientation at all other times.

Notably, the second cap 109 has both male 131 and female 133 couplings. This configuration allows the second cap 109 to couple with the container 103 by way of a male-female (cap-container) coupling when the sample canister 101 is in the first orientation as shown in FIG. 40, and to couple with the container 103 by way of a female-male (cap-container) coupling when the sample canister 101 is in the second orientation as shown in FIG. 41. This configuration prevents the exterior of the second cap 109, which may be exposed to contaminants (including biological materials containing DNA) during transportation, storage or use, from coming into contact with the interior surfaces of the container 103, where any contaminants left behind have a high risk of coming into contact with the swab 119 itself. By contrast, the prior art swab canister depicted in FIGS. 1-2 has a male-female (cap-container) coupling in both orientations, and thus does not avoid or address the foregoing contamination risk.

FIGS. 44-48 illustrate a second particular, non-limiting embodiment of a swab canister in accordance with the teachings herein. The swab canister 201 depicted therein is similar in many respects to the swab canister 101 of FIGS. 3-43, but differs in that it features a container 203 which is capped by a single cap 210 on a first end 205 thereof, and which is closed on the second end 207 thereof. As in the embodiment of FIGS. 3-43, this cap 210 has male 231 and female 233 couplings, which allow the swab canister 201 to be placed in the closed orientation shown in FIG. 44 through a male-female (cap-container) coupling, or in the open orientation shown in FIG. 46 through a female-male (cap-container) coupling. As in the previous embodiment, the open orientation is suitable for sample capture (and possibly sample analysis), while the closed orientation is suitable for most other purposes including, for example, storage and handling.

The cap 210 in swab canister 201 of FIGS. 44-48 essentially combines the functionalities of the caps 105, 107 in the swab canister 101 of FIGS. 3-43. Thus, in addition to supporting the sample collector 217 (which, in the embodiment depicted, comprises a portion of an absorbent material 219 such as cotton disposed on a wand 221), the cap 210 also has a portion of desiccant 213 disposed therein (which, in some embodiments, may be disposed in one or more packets). Preferably, the cap 210 contains an annular (or essentially annular) indentation around the base of male coupling element 231 in which the desiccant (which may be complimentary in shape to the annular indentation) is seated.

Figure 47:
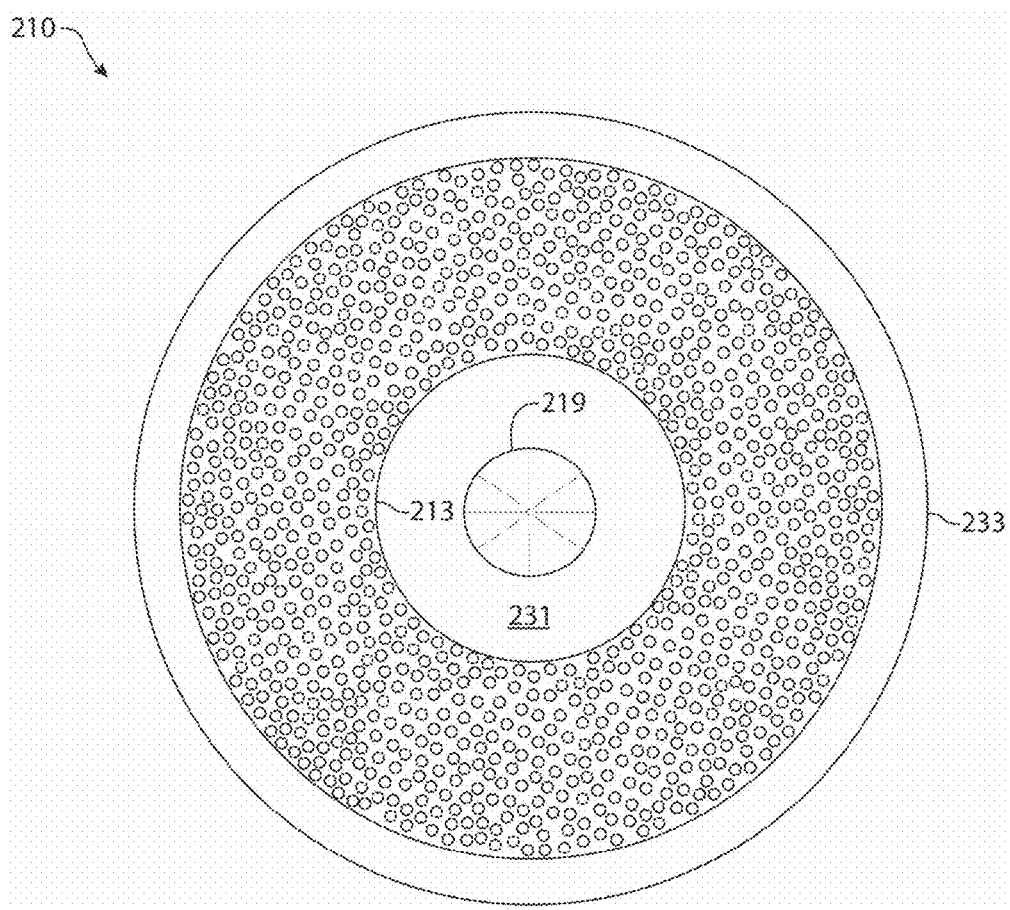
FIG. 47 is a bottom view of the cap of the swab canister of FIG. 44.
Figure 48:
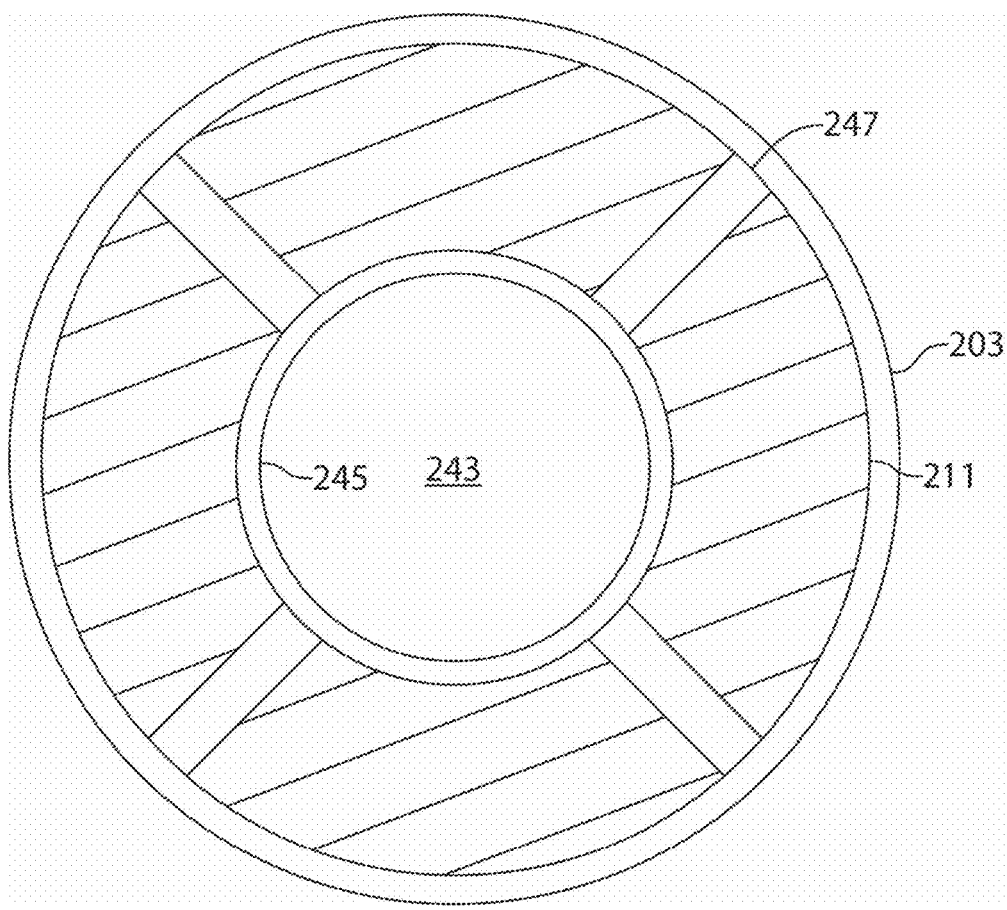
FIG. 48 is a top view of the cap of the swab canister of FIG. 44, shown with the cap removed.

The first end 205 of the container 203 is sealed with a membrane 211 similar to that in the first embodiment, and thus is preferably permeable to moisture and to a sanitizing agent (such as, for example, ethylene oxide) which is used to sanitize the interior surfaces of the swab canister 201 and to degrade any biological material thereon. As best seen in FIGS. 47-48, this membrane 211 is preferably annular (or essentially annular) in shape, and is equipped with a circular central opening 243 through which the male element 231 (see FIG. 44) extends. The central opening 243 is bounded by a collar 245 which may be supported, for example, by a plurality of struts 247 which extend radially away from the collar 245, and which may be connected to a peripheral element which is attached to, or pressingly engaged with, the interior surface of the container 203. When the swab canister 201 is in a closed configuration as in FIG. 44, the membrane 211 is disposed adjacent to the desiccant 213.

Figure 45:
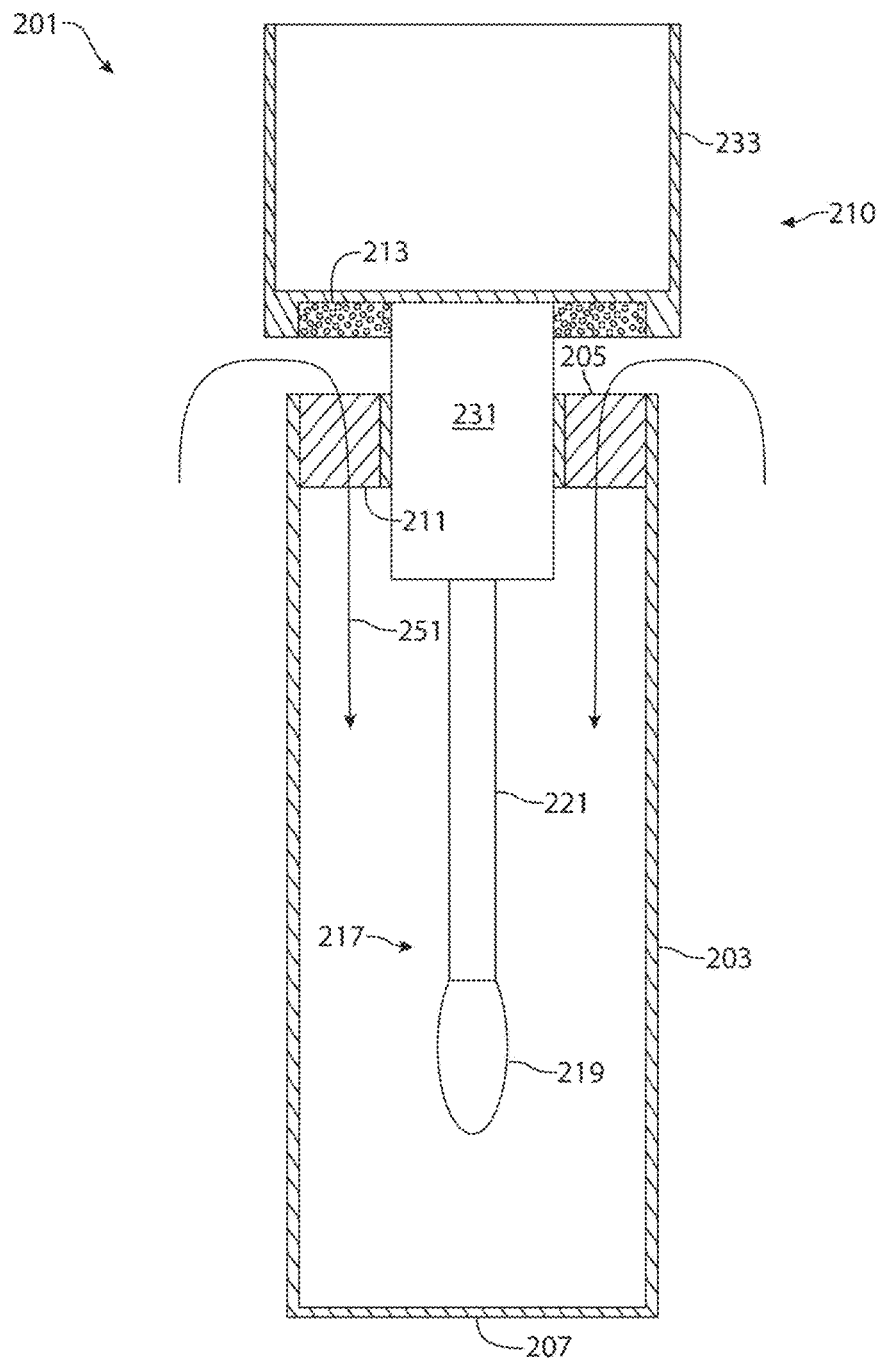
FIG. 45 is a perspective view of FIG. 44, depicting the swab canister in a semi-open configuration. In this configuration, the cap has been spaced apart from the container so that the canister is only open to the external environment by way of the water permeable membrane, thus allowing the canister to be sanitized (e.g., with ethylene oxide) without permitting the introduction of foreign contaminants.
Figure 46:
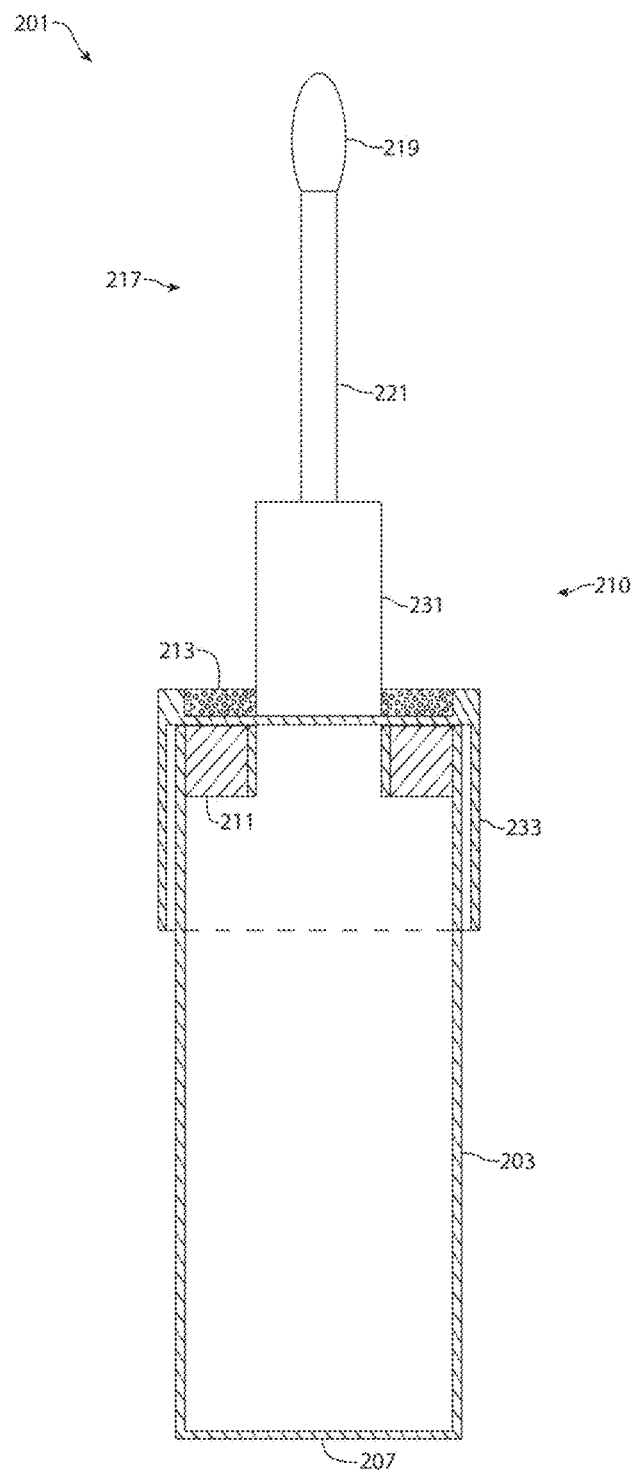
FIG. 46 is a perspective view of FIG. 44, depicting the swab canister in an open configuration and ready for use.

As seen in FIG. 45, the swab canister may be placed in a partially open configuration for sanitizing. In this orientation, the central opening 243 is still sealed by male member 231, but the interior surfaces of the swab canister 201 are in fluidic communication with the external environment by way of permeable membrane 211. This orientation allows the interior surfaces of the swab canister 201 to be sanitized with an agent, such as ethylene oxide, to which the membrane 211 is permeable. As previously noted, sanitization preferably occurs before addition of the desiccant 213 to the swab canister. Alternatively, in some embodiments, the desiccant may be chemically isolated from the sanitizing agent during this point in the process by way of, for example, a removable plastic sheet that is impermeable to the sanitizing agent.

Figure 49:
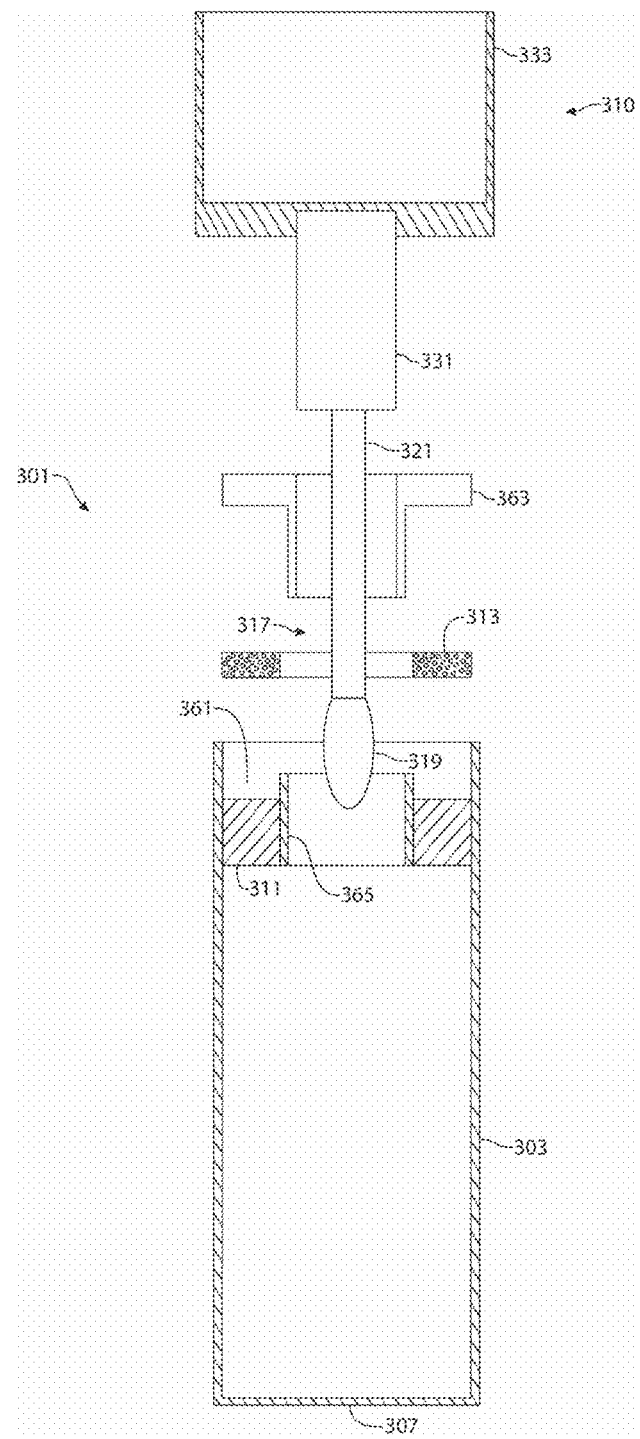
FIG. 49 is a perspective view of a third particular, non-limiting embodiment of a swab canister in accordance with the teachings herein.

FIG. 49 depicts a further particular, non-limiting embodiment of a swab canister 301 in accordance with the teachings herein. The swab canister 301 depicted therein is similar in many respects to the swab canister 201 of FIG. 48. However, in the swab canister 301 of FIG. 49, the first end 305 of the container 303 is equipped with an indentation 361 within which the desiccant 313 is seated. An optional cap 363 is provided which is seated on top of the desiccant 313.

During manufacture, the container 303 is sanitized while male coupling 331 is partially inserted into female opening 365, after which the cap 363 and desiccant 313 are installed in the container 303. This approach avoids undesirable interaction between the desiccant 313 and sanitizing agent, while allowing the interior of the container 303 to be sanitized. On the other hand, this embodiment allows the desiccant 313 to remain seated in the container 303 during sampling with the sampling collector 317, which may be advantageous in some applications.

It will be appreciated that various modifications are possible with the foregoing embodiment. For example, while the cap 363 and desiccant 313 are illustrated as separate components in FIG. 49, one skilled in the art will appreciate that, in variations of this embodiment, these components may be combined in to a unitary construct. Moreover, in some embodiments, the cap 363 may be dispensed with entirely, or replaced with a suitable (and preferably water impermeable) film. However, it is preferred that desiccant 313 and cap 363 are added around male coupling 331 such that the interior of container 303 is not exposed to the external environment after sanitization until use of the swab canister 301.

Various modifications may be made to the devices and methodologies disclosed herein without departing from the scope of the teachings herein. For example, the container used in the swab canisters described herein may have various geometries. In some embodiments, the container may be generally tubular in shape, with a cross-section taken perpendicular to its longitudinal axis which may be essentially polygonal (including, for example, square, rectangular, pentagonal, or hexagonal), elliptical, circular or irregular. However, the container preferably has at least one flattened surface to prevent the canister from rolling when it is placed on an uneven surface, and to provide a surface to which labeling may be applied as, for example, to identify the sample captured with the canister.

Moreover, while the devices and methodologies disclosed herein have frequently been described with reference to swab canisters, one skilled in the art will appreciate that the teachings of the present disclosure may be readily extended to other types of sample collectors or sample holders.

Various desiccants may be utilized in the devices and methodologies disclosed herein. The choice of desiccant may be driven by the particular application (or applications) to which a sample collector is directed. Suitable desiccants may include, but are not limited to, activated alumina, various aerogels, benzophenone, bentonite clay, calcium chloride, calcium sulfate, cobalt (II) chloride, copper (II) sulfate, lithium chloride, lithium bromide, magnesium sulfate, magnesium perchlorate, molecular sieves, potassium carbonate, potassium hydroxide, silica gel, sodium (typically only suitable in special applications), sodium chloride, sodium chloride, sodium hydroxide, sodium sulfate, sucrose, and various hygroscopic materials as are known to the art.

While ethylene oxide is the preferred sanitizing agent for use in the devices and methodologies described herein, it will be appreciated that various other sanitizing agents may be utilized as well, although the use of gaseous sanitizing agents is preferred. It will also be appreciated that the choice of membrane will typically depend on the choice of sanitizing agent (or vice versa). Possible gaseous sanitizing agents that may be utilized in the devices and methodologies described herein include, but are not limited to, ethylene oxide, nitrogen dioxide, ozone, hydrogen peroxide, and mixtures of the foregoing with each other and/or with diluent or carrier gases. Such diluent or carrier gases may include, for example, nitrogen, helium and argon.

In some embodiments, non-gaseous sanitizing agents may also be utilized (possibly in combination with any of the foregoing gaseous sanitizing agents) to sanitize the sample swabs and swab canisters described herein. Such non-gaseous sanitizing agents may include, for example, glutaraldehye, formaldehyde or peracetic acid solutions. Other sanitizing techniques may also be utilized including, but not limited to, the use of heat, steam, and radiation (including ionizing or non-ionizing radiation).

Various materials may be utilized in the swabs of the sample collectors described herein. Preferably, the materials utilized are absorbent, chemically unreactive materials, and the use of cotton is especially preferred. However, in some embodiments, other materials may be utilized instead of, or in addition to, cotton. Such other materials may include, for example, natural or synthetic polymeric materials, cellular plastics or foams, and the swabs may have flocked, viscose or alginate tips.

Various materials may also be used in the shafts of the sample collectors described herein. Thus, for example, the sample collectors may have aluminum, polypropylene, polystyrene or wooden shafts.

The above description of the present invention is illustrative, and is not intended to be limiting. It will thus be appreciated that various additions, substitutions and modifications may be made to the above described embodiments without departing from the scope of the present invention. Accordingly, the scope of the present invention should be construed in reference to the appended claims.

What is claimed is:
1. An apparatus, comprising:
a container equipped with a first opening, wherein said container has a removable sample collector disposed therein;
a membrane disposed between said sample collector and said first opening, wherein said membrane is permeable to both ethylene oxide and $H_2O$; and
a desiccant disposed between said membrane and said first opening.

2. The apparatus of claim 1, further comprising a first cap disposed over said first opening.

3. The apparatus of claim 2, wherein said container further comprises a second opening through which said sample collector is removed from said container.

4. The apparatus of claim 3, further comprising a second cap disposed over said second opening, wherein said second cap is removable from said second opening, and wherein said sample collector depends from said second cap.

5. The apparatus of claim 4, wherein said sample collector includes an absorbent medium mounted on a longitudinally extending arm.

6. The apparatus of claim 4, wherein said apparatus is transformable between a first configuration in which said second cap is releasably mated to said container and said sample collector is disposed within said container, and a second configuration in which said second cap is releasably mated to said container and said sample collector extends away from said container.

7. The apparatus of claim 6, wherein said second opening is a female opening, and wherein said second cap has a male surface which releasably couples with said second opening when said apparatus is in said first configuration.

8. The apparatus of claim 7, wherein said second cap has a female surface which releasably couples with said container when said apparatus is in said second configuration.

9. The apparatus of claim 7, wherein said male surface comprises a resilient material.

10. The apparatus of claim 7, wherein said second opening is equipped with a first set of threads, and wherein said second cap is equipped with a second set of threads which rotatingly engage said first set of threads.

11. The apparatus of claim 1, wherein said container is a parallelepiped.

12. The apparatus of claim 1, wherein said container has at least one flattened surface.

13. The apparatus of claim 1, wherein said container is equipped with a second opening, and wherein said first and second openings are disposed on opposing sides of said container.

14. The apparatus of claim 13, further comprising a first cap seated in said first opening, and a second cap removably seated in said second opening, and wherein said sample collector protrudes from said second cap.

15. An apparatus, comprising:
- a sample container having a removable sample collector disposed therein;
- a sealable desiccant chamber;
- a semi-permeable membrane disposed between, and maintaining fluid contact between, the container and the chamber;
- a desiccant insertable in the chamber; and
- a chamber lid that seals the chamber after desiccant insertion;
- wherein, during sanitizing, the interior of the container is accessible to at least one sanitizing agent through the membrane and the chamber.

16. An apparatus, comprising:
- a container which encloses an interior space, wherein said container has a flat exterior surface and is equipped with first and second openings on first and second opposing ends thereof;
- a first cap seated in said first opening, wherein said first cap is equipped with a membrane which is permeable to both ethylene oxide and $H_2O$, wherein said first cap has a desiccant disposed therein, and wherein said membrane is disposed between said desiccant and said interior space;
- a second cap removably seated in said second opening, wherein said second cap has a sample collector disposed thereon which protrudes into said interior space, and wherein said sample collector includes an absorbent medium mounted on a longitudinally extending arm.

17. The apparatus of claim 16, further comprising an ampule containing a liquid medium, wherein said ampule is disposed in said second cap.

18. The apparatus of claim 16, further comprising an ampule containing a liquid medium, wherein said ampule is releasably attached to said second cap.

19. The apparatus of claim 16, further comprising an ampule containing a liquid medium, wherein said ampule is equipped with a flattened tail, wherein said cap contains a slot, and wherein said tail is releasably inserted into said slot.

20. The apparatus of claim 17, wherein said liquid medium is selected from the group consisting of saline solutions and deionized water.

* * * * *